(12) United States Patent
Krijgsman et al.

(10) Patent No.: US 9,175,351 B2
(45) Date of Patent: Nov. 3, 2015

(54) MEANS AND METHODS FOR MOLECULAR CLASSIFICATION OF BREAST CANCER

(75) Inventors: Oscar Krijgsman, Almere (NL); Paul Roepman, Bilthoven (NL); Annuska Maria Glas, Assendelft (NL)

(73) Assignee: AGENDIA N.V., Amsterdam (NL)

( * ) Notice: Subject to any disclaimer, the term of this patent is extended or adjusted under 35 U.S.C. 154(b) by 22 days.

(21) Appl. No.: 13/546,755

(22) Filed: Jul. 11, 2012

(65) Prior Publication Data
US 2013/0178381 A1 Jul. 11, 2013

Related U.S. Application Data

(60) Provisional application No. 61/507,198, filed on Jul. 13, 2011.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/112* (2013.01); *C12Q 2600/158* (2013.01)

(58) Field of Classification Search
CPC .................................................. C12Q 1/6868
USPC ........................................................... 506/7
See application file for complete search history.

(56) References Cited

U.S. PATENT DOCUMENTS

| 6,204,375 B1 | 3/2001 | Lader |
| 7,138,226 B2 | 11/2006 | Vincek et al. |
| 2007/0072167 A1 | 3/2007 | Rochaix |
| 2008/0187909 A1* | 8/2008 | Dai et al. ........................ 435/6 |
| 2010/0209928 A1* | 8/2010 | Mirza et al. .................... 435/6 |
| 2011/0217297 A1* | 9/2011 | Kao et al. ................... 424/133.1 |
| 2011/0306572 A1* | 12/2011 | Estok et al. ..................... 514/49 |

FOREIGN PATENT DOCUMENTS

| DE | 10021390 A1 | 11/2001 |
| WO | WO 02/103320 A2 | 12/2002 |
| WO | WO 2004/083369 A2 | 9/2004 |
| WO | WO 2008/039071 A2 | 4/2008 |

OTHER PUBLICATIONS

Hu et al., Molecular Cancer Research, 2009, 7(4), pp. 511-522.*
de Ronde et al., Breast Cancer Research Treatment, 2010, 119, pp. 119-126.*
Dunnwald et al., Breast Cancer Research, 2007, 9, pp. 1-10.*
Affymentrix Data Sheet for GeneChip Human Genome Arrays, 2003-2004, pp. 1-4.*

(Continued)

*Primary Examiner* — Larry Riggs
*Assistant Examiner* — Karla Dines
(74) *Attorney, Agent, or Firm* — Hoffmann & Baron, LLP

(57) ABSTRACT

The invention relates to a method of typing a sample from a breast cancer patient. More specifically, the invention relates to a method for classification of breast cancer according to the presence or absence of Estrogen Receptor (ER), Progesterone Receptor (PR) and Human Epidermal growth facto Receptor 2 (ERBB2; HER2). More specifically, the invention Provides methods and means to classify breast cancer as ER positive, triple negative (ER$^-$, PR$^-$ and HER2$^-$) and HER2+.

14 Claims, 4 Drawing Sheets

(56) References Cited

OTHER PUBLICATIONS

Figure 1A:
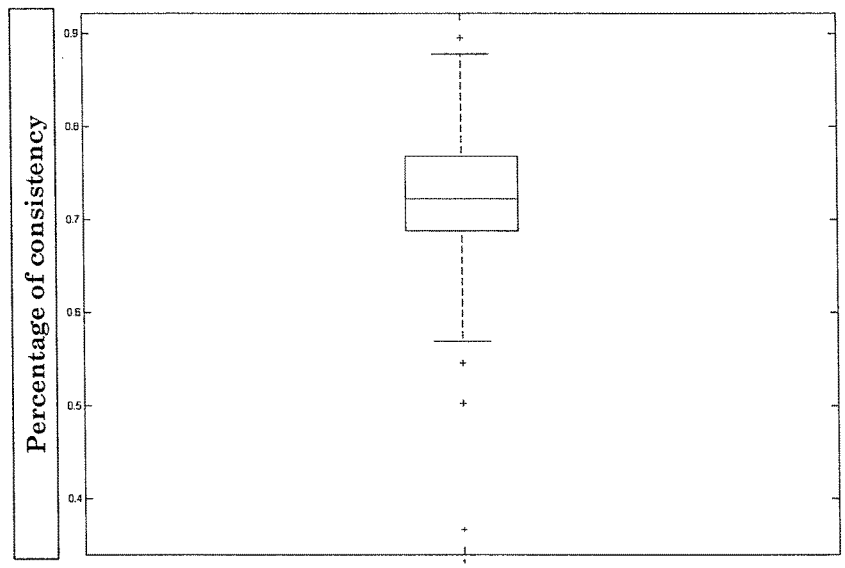

Anders, Carey, et. al., "Understanding and Treating Triple-Negative Breast Cancer", Oncology, Oct. 2008, 22:11, pp. 1233-1243.
Bertucci, François, et al., "How basal are triple-negative breast cancers?", Int. J. Cancer: 123, 236-240, (2008).
Bueno-de-Mesquita, Jolien, et al., "Use of 7-gene signature to predict prognosis of patients with node-negative breast cancer: a prospective community-based feasibility study (RASTER)", Lancet Oncol 2007;8:1079-87.
Carey, Lisa A., et al., "The Triple Negative Paradox: Primary Tumor Chemosensitivity of Breast Cancer Subtypes", Clin Cancer Res 2007;13:2329-2334.
Cheang, Maggie C.U., et al., "Ki67 Index, HER2 Status, and Prognosis of Patients With Luminal B Breast Cancer", J Natl Cancer Inst 2009;101:736-750.
Cheng, Fan, et al., "Concordance among Gene-Expression-Based Predictors for Breast Cancer", N Engl J Med 2006; 355:560-9.
Fisher, Bernard, et al., "Effect of Preoperative Chemotherapy on the Outcome of Women With Operable Breast Cancer", Journal of clinical Oncology, vol. 16, No. 8 Aug. 1998: pp. 2672-2685.
Garcia Pedrero, Juana M., et al., "The Naturally Occurring Variant of Estrogen Receptor (ER) ERAE7 Suppresses Estrogen-Dependent Transcriptional Activation by Both Wild-Type ERα and ERβ", Endocrinology, Jul. 2003, 144(7):2967-2976.
Glas, Annuska M., et al., "Gene expression profiling in follicular lymphoma to assess clinical aggressiveness and to guide the choice of treatment", Blood, Jan. 1, 2005, vol. 105, No. 1: 301-307.
Herynk, Matthew H., et al., "Estrogen Receptor Mutations in Human Disease", Endocrine Reviews, Dec. 2004, 25(6):869-898.
Hess, Kenneth R., et al., "Pharmacogenomic Predictor of Sensitivity to Preoperative Chemotherapy With Paclitaxel and Fluorouracil, Doxorubicin, and Cyclophosphamide in Breast Cancer", Journal of Clinical Oncology, vol. 24, No. 26, Sep. 10, 2006: pp. 4236-4244.
Kauraniemi, P., et al., "Activation of multiple cancer-associated genes at the ERBB2 amplicon in breast cancer", Endocrine-Related Cancer (2006) 13:39-49.
Kok, Fatma O., et al., "Churchill and Sip1a Repress Fibroblast Growth Factor Signaling During Zebrafish Somitogenesis", Developmental Dynamics 239:548-558, 2010.
Kuerer, Henry M., et al., "Clinical Course of Breast Cancer Patients With Complete Pathologic Primary Tumor and Axillary Lymph Node Response to Doxorubicin-Based Neoadjuvant Chemotherapy", Journal of Clinical Oncology, vol. 17, No. 2 Feb. 1999: pp. 460-469.
Liedtke, Cornelia, et al., "Response to Neoadjuvant Therapy and Long-Term Survival in Patients With Triple-Negative Breast Cancer", Journal of clinical Oncology, vol. 26, No. 8, Mar. 10, 2008: pp. 1275-1281.
Livasy, Chad A., et al., "Phenotypic evaluation of the basal-like subtype of invasive breast carcinoma", Modern Pathology (2006) 19, 264-271.
Martin-Magniette, Marie-Laure, et al., "Evaluation of the gene-specific dye bias in cDNA microarray experiments", Bioinformatics, vol. 21 No. 9 2005, pp. 1995-2000.

McShane, Lisa, et al., "Reporting Recommendations for Tumor Marker Prognostic Studies", Journal of Clinical Oncology, vol. 23, No. 36, Dec. 20, 2005: pp. 9067-9072.
Miller, Lance D., et al., "An expression signature for p53 status in human breast cancer predicts mutation status, transcriptional effects, and patient survival", PNAS, Sep. 20, 2005, vol. 102, No. 38, pp. 13550-13555.
Nielsen, Torsten O., et al., "Immunohistochemical and Clinical Characterization of the Basal-Like Subtype of Invasive Breast Carcinoma", Clinical Cancer Research, vol. 10. 5367-5374. Aug. 15, 2004.
Paik, Soonmyung, et al., "A Multigene Assay to Predict Recurrence of Tamoxifen-Treated, Node-Negative Breast Cancer", The New England Journal of Medicine, Dec. 30, 2004; 351;27:2817-26.
Parker, Joel S., et al., "Supervised Risk Predictor of Breast Cancer Based on Intrinsic Subtypes", Journal of Clinical Oncology, vol. 27, No. 8, Mar. 10, 2009, pp. 1160-1167.
Pawitan, Yudi, et al., "Gene expression profiling spares early breast cancer patients from adjuvant therapy: derived and validated in two population-based cohorts", Breast Cancer Research 2005, vol. 7, No. 6:R953-R964.
Perou, Charles M., et al., "Molecular portraits of human breast tumours", Nature, vol. 406, Aug. 17, 2000, pp. 747-752.
Rakha, Emad A., et al., "Basal-Like Breast Cancer: A Critical Review", Journal of Clinical Oncology, vol. 26, No. 15, May 20, 2008, pp. 2568-2581.
Rakha, Emad A., et al., "Triple-Negative Breast Cancer: Distinguishing between Basal and Nonbasal Subtypes", Clinical Cancer Research, Apr. 1, 2009;15(7):2302-2310.
Rastogi, Priya, et al., "Preoperative Chemotherapy: Updates of National Surgical Adjuvant Breast and Bowel Project Protocols B-18 and B-27", Journal of Clinical Oncology, vol. 26, No. 5, Feb. 10, 2008, pp. 778-785.
Roepman, Paul, et al., "Microarray-Based Determination of Estrogen Receptor, Progesterone Receptor, and HER2 Receptor Status in Breast Cancer", Clinical Cancer Research, Nov. 15, 2009;15(22):7003-7011.
Rouzier, Roman, et al., "Breast Cancer Molecular Subtypes respond Differently to Preoperative Chemotherapy", Clinical Cancer Research, Aug. 15, 2005; 11(16):5678-5685.
Sørlie, Therese, et al., "Gene expression patterns of breast carcinomas distinguish tumor subclasses with clinical implications", PNAS, Sep. 11, 2001, vol. 98, No. 19:10869-10874.
Straver, Marieke E., et al., "The 70-gene signature as a response predictor for neoadjuvant chemotherapy in breast cancer", Breast Cancer Res Treat (2010) 119:551-558.
Van 'T Veer, Laura J., et al., "Gene expression profoling predicts clinical outcome of breast cancer", Nature, vol. 415, Jan. 31, 2002, pp. 530-536.
Vijver van de, Marc J., et al., "A Gene-Expression Signature as a Predictor of Survival in Breast Cancer", The New England Journal of Medicine, vol. 347, Dec. 19, 2002, No. 25:1999-2009.
Yang, Yee Hwa., et al., "Normalization for cDNA microarray data: a robust composite method addressing single and multiple slide systematic variation", Nucleic Acids Research, 2002, vol. 30, No. 4 e15.
Liang, Hongyan, et al., "Iniparib, a PARP1 inhibitor for the potential treatment of cancer, including triple-negative breast cancer", IDrugs 2010 13(9):646-656.

\* cited by examiner

Percentage of constant subtype assignments by random combination of 2 genes from each of Tables 1A-1C Percentage of constant subtype assignments by random combination of 3 genes from each of Tables 1A-1C

MEANS AND METHODS FOR MOLECULAR CLASSIFICATION OF BREAST CANCER

CROSS-REFERENCE TO RELATED APPLICATIONS

This application claims the benefit of priority from U.S. Provisional Patent Application No. 61/507,198 filed Jul. 13, 2011, the disclosure of which is incorporated herein by reference.

INCORPORATION OF SEQUENCE LISTING

Incorporated herein in its entirety and submitted herewith is the computer readable Sequence Listing for the above-identified Application. The Sequence Listing is disclosed on a computer-readable ASCII text file titled "SequenceListing294-411.txt", date modified on Jul. 11, 2012. The sequence.txt file is 8.79 KB size.

FIELD OF THE INVENTION

The invention relates to the field of oncology. More specifically, the invention relates to a method for typing breast cancer cells. The invention provides means and methods for molecular classification of breast cancer cells.

BACKGROUND OF THE INVENTION

Background of the invention: Recent studies have shown that the classification of breast cancer into molecular subtypes is largely represented by the Estrogen Receptor (ER), Progesterone Receptor (PR) and Human Epidermal growth factor Receptor 2 (HER2) status of the tumor: Basal-like breast cancers correlate best with ER-negative, PR-negative, and HER2-negative tumors [Rakha et al. Clin Cancer Res 2009, 15:2302-2310; Carey et al. 2007. Clin Cancer Res 2007, 13:2329-2334]. Luminal-like cancers are ER-positive [Nielsen et al. Clin Cancer Res 2004, 10:5367-5374] and HER2- positive cancers have a high expression of the HER2 gene [Kauraniemi and Kallioniemi. Endocr Relat Cancer 2006, 13:39-49]. Breast cancer can be classified into molecular subtypes by simple hierarchical clustering of breast tumors according to their gene expression patterns [Perou et al. Nature 2000, 406:747-752]. While this classification system has been developed without consideration of patient survival rates, the different molecular subtypes of breast cancer have different prognoses: luminal-like tumors have a more favorable outcome and basal-like and HER2 subgroups are more sensitive to chemotherapy [Sorlie et al. Proc Natl Acad Sci USA 2001, 98:10869-10874; Rouzier et al. Clin Cancer Res 2005, 11(16):5678-5685; Liedtke et al. J Clin Oncol 2008, 26(8):1275-1281]. To date, molecular classification has not played a major role in treatment decisions. However, given the role that these subtypes have played in clinical trials (e.g. PARP inhibitors or platinum agents and taxanes for triple negative cancers [Rakha et al. J Clin Oncol 2008, 26:2568-2581; Liang et al. Drugs 2010, 13(9):646-656]) they are likely to play an important role in future clinical practice.

Concordance between the status of a receptor as determined by immunohistochemistry (IHC) and the molecular subtype suggests that molecular profiles represent oncogenic processes that are driven by pathways in which ER, PR and HER2 play pivotal roles [Carey et al. 2007. Clin Cancer Res 2007, 13:2329-2334; Nielsen et al. Clin Cancer Res 2004, 10:5367-53742,3, Sotiriou and Pusztai. N Engl J Med 2009, 360(8):790-800; Cheang et al. J Natl Cancer Inst 2009, 101 (10):736-750; Livasy et al. Mod Pathol. 2006, 19(2):264-271]. It is, therefore, likely that the use of gene expression arrays will enable the identification of previously unappreciated subtypes of breast cancer that differ in clinical outcomes.

Molecular classification of breast tumors by IHC or through determination of gene activity by measuring mRNA levels for single genes rely on the presence of protein and mRNA respectively, but neither assay determines whether that protein or mRNA is functional in making full length and functional receptor proteins. As such, both methods have an inherent uncertainty in predicting whether a tumor is truly positive for functional ER, PR or HER2 protein [Roepman et al. Clin Cancer Res 2009, 15(22):7004-7011]. One method to circumvent this problem is to develop gene signatures that measure the expression of groups of genes that correlate with the presence and activity of the gene(s) of interest [van 't Veer et al. Nature 2002, 415:530-536; Paik et al. N Engl J Med 2004, 351(27):2817-2826]. A gene profile that is indicative of the activity of ER, PR and/or HER2 would allow the molecular classification of breast tumors by characterization of the functional activity of these genes.

SUMMARY OF THE INVENTION

The present inventors have now developed a gene profile that is indicative of the activity of ER, PR and/or HER2 in a breast tumor cell. Methods of typing a sample from a breast cancer patient according to the presence or absence of activity of ER, PR and/or HER2, comprise determining the level of expression of genes from the gene profile.

The gene profile was identified after careful classification of breast tumor samples according to the analysis of ER, PR and HER2 expression on the RNA level by microarray-based single gene readout and on the protein level by immunohistochemistry (IHC). Only breast tumor samples in which both types of analyses yielded the same result, namely presence or absence of expression of ER, PR and/or HER2 on both the mRNA level as well as on the protein level, were used to identify genes that are indicative for the presence or absence of ER, PR and/or HER2.

The present invention provides a method of typing a sample from a breast cancer patient, the method comprising determining a level of RNA expression for at least two genes that are selected from Table 1A, at least two genes that are selected from Table 1B, and at least two genes that are selected from Table 1C, in a relevant sample from the breast cancer patient, whereby the sample comprises RNA expression products from a cancer cell of the patient, comparing said determined level of RNA expression of the at least six genes to the level of expression of the genes in a reference sample and typing said sample based on the comparison of the determined levels of RNA expression. Typing of a breast tumor sample according to a method of the invention will classify that sample as ER+ like, triple-negative like, or HER2+ like.

In a preferred method of the invention, at least one of the at least two genes selected from Table 1A is a gene that is upregulated in a ER+ breast cancer and at least one further gene is downregulated in a ER+ breast cancer, compared to the level of expression in the reference sample. In a further preferred method of the invention, at least one of the at least two genes selected from Table 1B is a gene that is upregulated in a triple-negative breast cancer and at least one further gene is downregulated in a triple-negative breast cancer, compared to the level of expression in the reference sample. Yet in a further preferred method at least one of the at least two genes selected from Table 1C is a gene that is upregulated in a HER2+ breast cancer and at least one further gene is downregulated in a HER2+ breast cancer, compared to the level of expression in the reference sample.

In a further preferred method according to the invention, a level of RNA expression of at least five genes from Table 1A, and/or at least five genes from Table 1B, and/or all three genes from Table 1C is determined.

In a further embodiment, a method according to the invention further comprises determining a metastasizing potential of the sample from the patient. Said metastasizing potential is preferably determined by a 70 gene profile (MammaPrint®), as described in WO2002/103320.

In yet a further embodiment, a method according to the invention further comprises determining a strategy for treatment of the patient. A preferred method of assigning treatment to a patient suffering from breast cancer, comprises:
(a) typing a relevant sample from the patient according to a method of the invention;
(b) classifying said sample as a ER+, triple negative, or HER2+;
(c) assigning treatment to an individual of which the sample is classified as triple negative or HER2+.

A further preferred method of assigning treatment to a patient suffering from breast cancer, comprises:
(a) typing a relevant sample from the patient according to a method of the invention;
(b) classifying said sample as a ER+, triple negative, or HER2+;
(c) assigning anti-estrogen therapy if the sample is classified as a ER+.

LEGENDS TO FIGURES

FIG. 1 Correlation of subtype assignment by a random combination of 2 genes (1A) or three genes from each of Tables 1A-1C.

Figure 2:
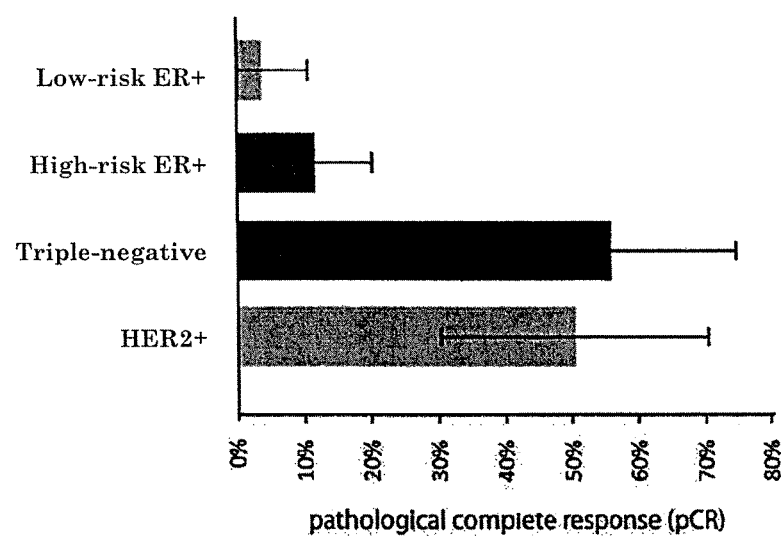

FIG. 2 Chemotherapy response differs among the MSP classes.

Pathological Complete Response (pCR) rates are shown for cohort 6 MammaPrint low-risk/ER+, MammaPrint high-risk/ER+, triple negative and HER2+ breast cancers. Error bars indicate the 95% CI for the corresponding pCR proportions.

Figure 3:
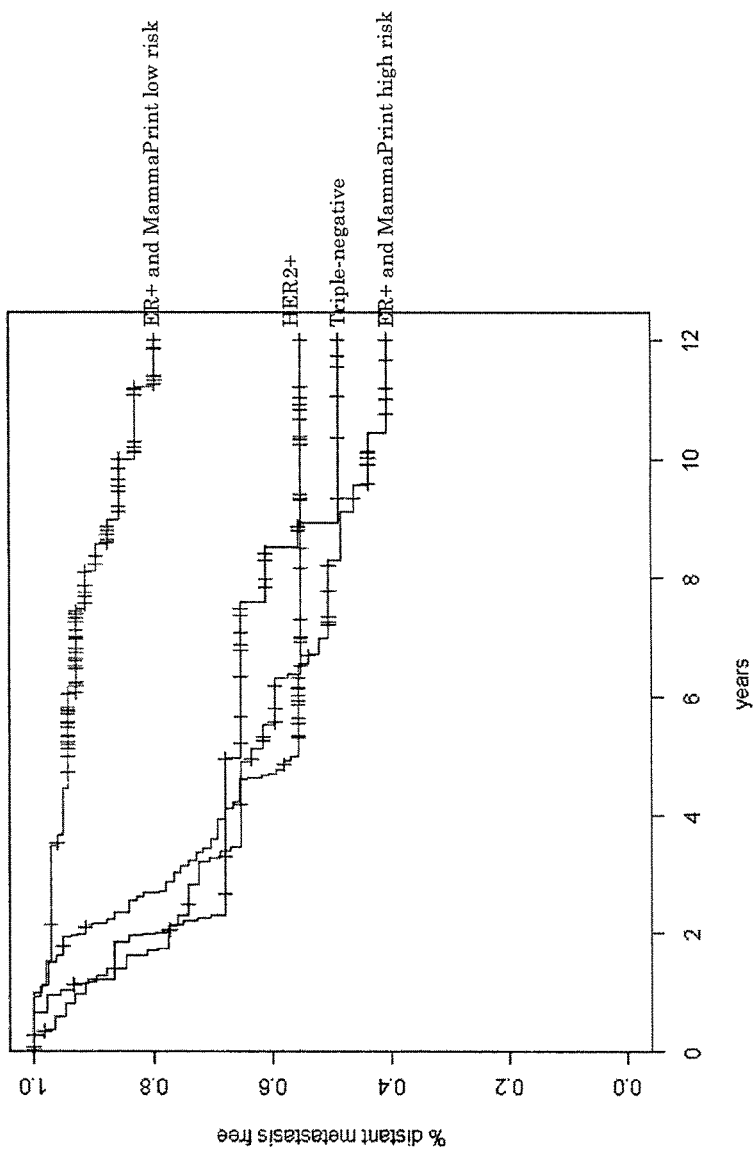

FIG. 3 Survival analysis of the NEJM samples classified using the MSC. Survival was plotted over a period of 12 years.

Figure 4:
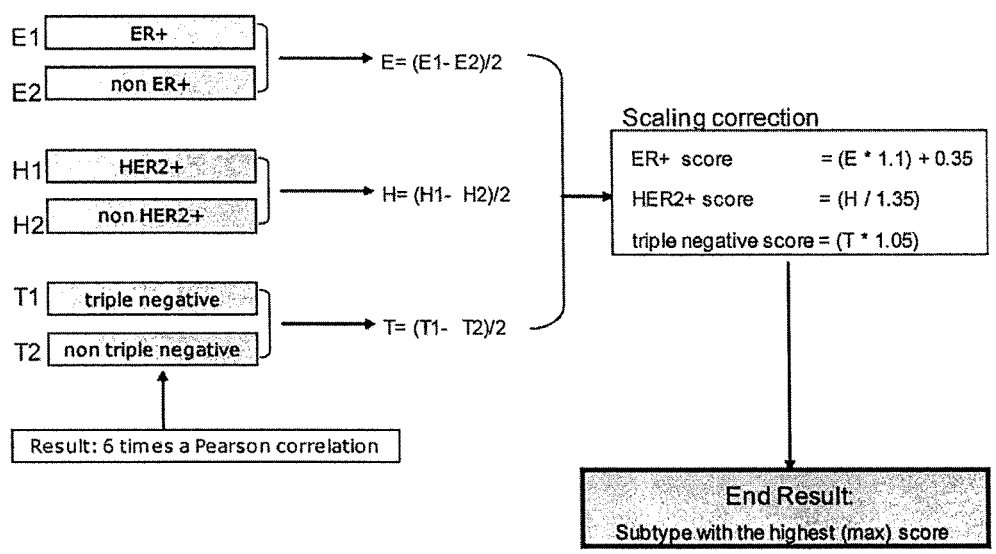

FIG. 4. Calculation of index score.

DETAILED DESCRIPTION OF THE INVENTION

The present inventors have developed a gene profile, termed Molecular Subtyping Profile (MSP) that is indicative of the activity of estrogen receptor (ER), progesterone receptor (PR) and/or Human Epidermal growth factor Receptor 2 (HER2) in a breast tumor cell. Methods of typing a sample from a breast cancer patient according to the presence or absence of activity of ER, PR and/or HER2, comprise determining the level of expression of genes from the gene profile, as indicated in Table 1. The methods of the invention allow classifying a breast cancer sample that was determined to be estrogen receptor positive by immunohistochemistry (IHC) as ER− in cases where the ER is defective. Therefore, MSP allows the phenotypical classification of the ER, PR and/or HER2 status in a breast cancer sample, in contrast to the genotypical classification that is provided by IHC.

The genes depicted in Table 1 were identified in a multistep analysis of samples from breast cancer patients. In a first step, 295 breast cancer samples were classified according to the expression of ER, PR and HER2, both by immunohistochemistry (IHC) and by RNA-expression analysis (TargetPrint®). The 200 samples from which the IHC data agreed with the RNA expression data were divided into triple negative (ER−, PR−, and HER2−), ER+, and HER2+. Subsequently, genes were identified of which the relative level of expression is indicative for one of the three molecular subtypes. The term relative is used to indicate that the level of expression was compared to the level of expression in a reference sample, in this case pooled breast cancer samples. The expression of each of the genes depicted in Table 1 correlates with one of the three molecular subtypes. For example, upregulation of NM_000060 (BTD) and downregulation of NM_001124 (ADM), compared to a reference sample, is indicative of a ER+ breast cancer molecular subtype. Upregulation of NM_002444 (MSN) and downregulation of NM_001267 (CHAD) is indicative of a triple-negative breast cancer molecular subtype. Upregulation of NM_033419 (PERLD1) and downregulation of NM_153694 (SYCP3) is indicative of a HER2+ breast cancer molecular subtype. A sample comprising RNA expression products from a cancer cell of a breast cancer patient is provided after the removal of all or part of a breast cancer sample from the patient during surgery biopsy. For example, a sample comprising RNA may be obtained from a needle biopsy sample or from a tissue sample comprising breast cancer cells that was previously removed by surgery. The surgical step of removing a relevant tissue sample, in this case a breast cancer sample, from an individual is not part of a method according to the invention.

A sample from a breast cancer patient comprising RNA expression products from a tumor of the patient can be obtained in numerous ways, as is known to a skilled person. For example, the sample can be freshly prepared from cells or a tissue sample at the moment of harvesting, or it can be prepared from samples that are stored at −70° C. until processed for sample preparation. Alternatively, tissues or biopsies can be stored under conditions that preserve the quality of the protein or RNA. Examples of these preservative conditions are fixation using e.g. formaline and paraffin embedding, RNase inhibitors such as RNAsin® (Pharmingen) or RNasecure® (Ambion), aquous solutions such as RNAlater® (Assuragen; U.S. Pat. No. 6,204,375), Hepes-Glutamic acid buffer mediated Organic solvent Protection Effect (HOPE; DE10021390), and RCL2 (Alphelys; WO04083369), and non-aquous solutions such as Universal Molecular Fixative (Sakura Finetek USA Inc.; U.S. Pat. No. 7,138,226).

RNA may be isolated from a breast tissue sample comprising breast cancer cells by any technique known in the art, including but not limited to Trizol (Invitrogen; Carlsbad, Calif.), RNAqueous® (Applied Biosystems/Ambion, Austin, Tx), Qiazol® (Qiagen, Hilden, Germany), Agilent Total RNA Isolation Lits (Agilent; Santa Clara, Calif.), RNA-Bee® (Tel-Test. Friendswood, Tex.), and Maxwell™ 16 Total RNA Purification Kit (Promega; Madison, Wis.). A preferred RNA isolation procedure involves the use of Qiazol® (Qiagen, Hilden, Germany). RNA can be extracted from a whole sample or from a portion of a sample generated by, for example section or laser dissection.

The level of RNA expression of a signature gene according to the invention can be determined by any method known in the art. Methods to determine RNA levels of genes are known to a skilled person and include, but are not limited to, Northern blotting, quantitative Polymerase chain reaction (qPCR), also termed real time PCR (rtPCR), microarray analysis and RNA sequencing. The term qPCR refers to a method that allows amplification of relatively short (usually 100 to 1000 basepairs) of DNA sequences. In order to measure messenger RNA (mRNA), the method is extended using reverse transcriptase to convert mRNA into complementary DNA (cDNA) which is then amplified by PCR. The amount of product that is amplified can be quantified using, for example, TaqMan® (Applied Biosystems, Foster City, Calif., USA), Molecular Beacons, Scorpions® and SYBR® Green (Molecular Probes). Quantitative Nucleic acid sequence based amplification (qNASBA) can be used as an alternative for qPCR.

A preferred method for determining a level of RNA expression is microarray analysis. For microarray analysis, a hybridization mixture is prepared by extracting and labelling of RNA. The extracted RNA is preferably converted into a labelled sample comprising either complementary DNA (cDNA) or cRNA using a reverse-transcriptase enzyme and labelled nucleotides. A preferred labelling introduces fluorescently-labelled nucleotides such as, but not limited to, cyanine-3-CTP or cyanine-5-CTP. Examples of labelling methods are known in the art and include Low RNA Input Fluorescent Labelling Kit (Agilent Technologies), MessageAmp Kit (Ambion) and Microarray Labelling Kit (Stratagene).

A labelled sample preferably comprises two dyes that are used in a so-called two-colour array. For this, the sample is split in two or more parts, and one of the parts is labelled with a first fluorescent dye, while a second part is labelled with a second fluorescent dye. The labelled first part and the labelled second part are independently hybridized to a microarray. The duplicate hybridizations with the same samples allow compensating for dye bias.

More preferably, a sample is labelled with a first fluorescent dye, while a reference sample, for example a sample from a breast cancer pool or a sample from a relevant cell line or mixture of cell lines, is labelled with a second fluorescent dye. The labelled sample and the labelled reference are co-hybridized to a microarray. Even more preferred, a sample is labelled with a fluorescent dye and hybridized to a microrray without a reference sample.

The labelled sample can be hybridized against the probe molecules that are spotted on the array. A molecule in the labelled sample will bind to its appropriate complementary target sequence on the array. Before hybridization, the arrays are preferably incubated at high temperature with solutions of saline-sodium buffer (SSC), Sodium Dodecyl Sulfate (SDS) and bovine serum albumin (BSA) to reduce background due to nonspecific binding.

The arrays are preferably washed after hybridization to remove labelled sample that did not hybridize on the array, and to increase stringency of the experiment by reducing cross hybridization of the labelled sample to a partial complementary probe sequence on the array. An increased stringency will substantially reduce non-specific hybridization of the sample, while specific hybridization of the sample is not substantially reduced. Stringent conditions include, for example, washing steps for five minutes at room temperature 0.1× Sodium chloride-Sodium Citrate buffer (SSC)/0.005% Triton X-102. More stringent conditions include washing steps at elevated temperatures, such as 37 degrees Celsius, 45 degrees Celsius, or 65 degrees Celsius, either or not combined with a reduction in ionic strength of the buffer to 0.05×SSC or 0.01×SSC as is known to a skilled person.

Image acquisition and data analysis can subsequently be performed to produce an image of the surface of the hybridised array. For this, the slide can be dried and placed into a laser scanner to determine the amount of labelled sample that is bound to a target spot. Laser excitation yields an emission with characteristic spectra that is indicative of the labelled sample that is hybridized to a probe molecule. In addition, the amount of labelled sample can be quantified.

The level of expression, preferably mRNA expression levels of genes depicted in Table 1, is preferably compared to levels of expression of the same genes in a reference sample. A reference sample is preferably an RNA sample isolated from a tissue of a healthy individual, preferably comprising breast cells. A preferred reference sample comprises a RNA sample from a relevant cell line or mixture of cell lines. The RNA from a cell line or cell line mixture can be produced in-house or obtained from a commercial source such as, for example, Stratagene Human Reference RNA. A further preferred reference sample comprises RNA isolated and pooled from normal adjacent tissue from cancer patients, preferably breast cancer patients.

A more preferred reference sample comprises an RNA sample from an individual suffering from breast cancer, more preferred from multiple individuals suffering from breast cancer. It is preferred that said multiple samples are pooled from more than 10 individuals, more preferred more than 20 individuals, more preferred more than 30 individuals, more preferred more than 40 individuals, most preferred more than 50 individuals. A most preferred reference sample comprises a pooled RNA sample that is isolated from tissue comprising breast cancer cells from multiple individuals suffering from breast cancer.

As an alternative, a static reference can be generated which enables performing single channel hybridizations for this test. A preferred static reference is calculated by measuring the median background-subtracted level of expression (rMeanSignal) of a gene across 5 hybridizations of a reference sample, preferably obtained from pooled breast cancer samples, on a microarray. The level of expression may be normalized as is known a skilled person. Subsequently, log-ratios for each gene/probe hybridization is generated relative to the value of the static reference.

Typing of a sample can be performed in various ways. In one method, a coefficient is determined that is a measure of a similarity or dissimilarity of a sample with said reference sample. A number of different coefficients can be used for determining a correlation between the RNA expression level in an RNA sample from an individual and a reference sample. Preferred methods are parametric methods which assume a normal distribution of the data.

The result of a comparison of the determined expression levels with the expression levels of the same genes in at least one reference sample is preferably displayed or outputted to a user interface device, a computer readable storage medium, or a local or remote computer system. The storage medium may include, but is not limited to, a floppy disk, an optical disk, a compact disk read-only memory (CD-ROM), a compact disk rewritable (CD-RW), a memory stick, and a magneto-optical disk.

The expression data are preferably normalized. Normalization refers to a method for adjusting or correcting a systematic error in the measurements of detected label. Systemic bias results in variation by inter-array differences in overall performance, which can be due to for example inconsistencies in array fabrication, staining and scanning, and variation between labeled RNA samples, which can be due for example to variations in purity. Systemic bias can be introduced during the handling of the sample in a microarray experiment.

To reduce systemic bias, the determined RNA levels are preferably corrected for background non-specific hybridization and normalized using, for example, Feature Extraction software (Agilent Technologies). Other methods that are or will be known to a person of ordinary skill in the art, such as a dye swap experiment (Martin-Magniette et al., Bioinformatics 21:1995-2000 (2005)) can also be applied to normalize differences introduced by dye bias. Normalization of the expression levels results in normalized expression values.

Conventional methods for normalization of array data include global analysis, which is based on the assumption that the majority of genetic markers on an array are not differentially expressed between samples [Yang et al., Nucl Acids Res 30: 15 (2002)]. Alternatively, the array may comprise specific probes that are used for normalization. These probes preferably detect RNA products from housekeeping genes such as glyceraldehyde-3-phosphate dehydrogenase and 18S rRNA levels, of which the RNA level is thought to be constant in a given cell and independent from the developmental stage or prognosis of said cell.

Therefore, a preferred method according to the invention further comprises normalizing the determined RNA levels of said set of at least ten of the genes listed in Table 1 in said sample.

Said normalization preferably comprises median centering, in which the "centers" of the array data are brought to the same level under the assumption that the majority of genes are not changed between conditions. Said normalization preferably comprises Lowess (LOcally WEighted Scatterplot Smoothing) local regression normalization to correct for both print-tip and intensity-dependent bias.

In a preferred embodiment, genes are selected of which the RNA expression levels are largely constant between individual tissue samples comprising cancer cells from one individual, and between tissue samples comprising cancer cells from different individuals. It will be clear to a skilled artisan that the RNA levels of said set of normalization genes preferably allow normalization over the whole range of RNA levels. An example of a set of normalization genes is provided in WO 2008/039071, which is hereby incorporated by reference.

The levels of expression of genes from the MSP signature in a sample of a patient are compared to the level of expression of the same genes in a ER+ breast cancer sample, in a triple-negative breast cancer sample, and in a HER2+ breast cancer sample. Said comparison may result in an index score indicating a similarity of the determined expression levels in a sample of a patient with the expression levels in a ER+ breast cancer sample, in a triple-negative breast cancer sample, and in a HER2+ breast cancer sample. For example, an index can be generated by determining a Pearson correlation between the expression levels of the genes in a sample of a patient and the expression levels in a sample of an ER+ breast cancer and the average expression levels in non-ER+ breast cancer sample, i.e., triple negative and HER2+ breast cancer samples. Subsequently, the non-ER correlation is subtracted from the ER correlation. The same approach is applied by determining a Pearson correlation between the expression levels of the genes in a sample of a patient and the expression levels in a sample of a triple negative breast cancer and the average expression levels in non-triple negative breast cancer samples (ER+ and HER2+), and by determining a Pearson correlation between the expression levels of the genes in a sample of a patient and the expression levels in a sample of a HER2+ breast cancer and the average expression levels in non-HER2+ breast cancer samples (ER+ and triple-negative). The resultant Pearson scores can be used to provide an index score, for example as indicated in FIG. 4. Finally, the Blue-Print outcome will be represented by the subtype that has the highest index/score.

Said score may vary between +1, indicating a prefect similarity, and −1, indicating a reverse similarity. Preferably, an arbitrary threshold is used to type samples as ER+ breast cancer, triple-negative breast cancer or HER2+ breast cancer. More preferably, samples are classified as ER+, cancer, triple-negative, or HER2+ breast cancer based on the respective highest similarity measurement. A similarity score is preferably displayed or outputted to a user interface device, a computer readable storage medium, or a local or remote computer system.

A breast cancer patient is a patient that suffers, or is expected to suffer, from breast cancer. A preferred breast cancer is a ductal carcinoma in situ, a lobular carcinoma in situ, ductal carcinoma, an inflammatory carcinoma and/or a lobular carcinoma. A method according to the invention preferably further comprises assessment of clinical information, such as tumor size, tumor grade, lymph node status and family history. Clinical information may be determined in part by histopathological staging. Histopathological staging involves determining the extent of spread through the layers that form the lining of the duct or lobule, combined with determining of the number of lymph nodes that are affected by the cancer, and/or whether the cancer has spread to a distant organ. A preferred staging system is the TNM (for tumors/nodes/metastases) system, from the American Joint Committee on Cancer (AJCC). The TNM system assigns a number based on three categories. "T" denotes the size of the tumor, "N" the degree of lymphatic node involvement, and "M" the degree of metastasis. The method described here is stage independent and applies to all breast cancers.

It is preferred that at least one of the at least two genes selected from Table 1A is a gene that is upregulated in a ER+ breast cancer and at least one further gene is downregulated in a ER+ breast cancer, compared to the level of expression in the reference sample. Said upregulated gene is preferably selected from NPY1R, TPRG1, SUSD3, CCDC74B, CHAD, GREB1, PARD6B, PREX1, GOLSYN and ACADSB. Said downregulated gene is preferably selected from ADM, SOX11, CDC25B, LILRB3, and HK3. The at least one of the at least two genes selected from Table 1B is preferably a gene that is upregulated in a triple-negative breast cancer and at least one further gene is downregulated in a triple-negative breast cancer, compared to the level of expression in the reference sample. Said upregulated gene is preferably MSN. Said downregulated gene is preferably selected from PRR15, ABCC11, DHRS2, TBC1D9, GREB1, THSD4, CHAD, and PERLD1. The at least one of the at least two genes selected from Table 1C is preferably a gene that is upregulated in a triple-negative breast cancer and at least one further gene is downregulated in a triple-negative breast cancer, compared to the level of expression in the reference sample. Said upregulated gene is preferably PERLD1. Said downregulated gene is preferably SYCP3.

A further preferred method according to the invention comprises determining a level of RNA expression of at least three genes, more preferred at least five genes, more preferred at least 10 genes, more preferred at least twenty genes, more preferred all 35 genes from Table 1A. A further preferred method according to the invention comprises determining a level of RNA expression of at least three genes, more preferred at least five genes, more preferred at least 10 genes, more preferred all 13 genes from Table 1B. Yet a further preferred method comprises determining a level of RNA expression of all three genes from Table 1C.

Yet a further preferred method according to the invention comprises determining a level of RNA expression of the genes that are listed in Table 3.

Yet a further preferred method according to the invention comprises in addition to determining a level of RNA expression of at least two genes that are selected from Table 1A, at least two genes that are selected from Table 1B, and at least two genes that are selected from Table 1C, determining a level of RNA expression of one or more genes that are selected from Table 6. The genes depicted in Table 6 were selected because their level of expression significantly correlated (indicated as positive in Table 6) or anti-correlated (indicated as negative in Table 6) with the level of expression of HER2.

Yet a further preferred method according to the invention further comprises determining a metastasizing potential of the sample from the patient. Said metastasizing potential is preferably determined by molecular expression profiling. Molecular expression profiling may be used in stead of clinical assessment or, preferably, in addition to clinical assessment. Molecular expression profiling may facilitate the identification of patients who may be safely managed without adjuvant chemotherapy. A preferred molecular expression profiling is described in WO2002/103320, which is incorporated herein by reference. WO2002/103320 describes a molecular signature comprising at least 5 genes from a total of 231 genes that are used for determining a risk of recurrence of the breast cancer. A further preferred molecular signature that is described in WO2002/103320 provides a molecular signature comprising a subset of 70 genes from the 231 genes, as depicted in Table 6 of WO2002/103320. Further preferred molecular signatures include an 21-gene recurrence score (Paik et al. N Engl J. Med. 2004; 351:2817-2826) and Mammostrat™ (The Molecular Profiling Institute). A most preferred method for determining a metastasizing potential of breast cancer is a 70 gene profile (MammaPrint®) as described in Table 6 of WO2002/103320, which is incorporated herein by reference.

In yet a further aspect, the invention relates to a method for assigning treatment to a breast cancer patient, comprising the method for prognosing the risk of distant metastasis of breast cancer and assigning a strategy for treatment to the patient based on the prognosis.

The invention further provides a method of typing a sample from a breast cancer patient according to the invention, the method further comprising classifying said sample as a ER+, triple negative, or HER2+; and assigning treatment to an individual of which the sample is classified as triple negative or HER2+. Triple negative breast cancer is typically treated with a combination of therapies such as surgery, radiation therapy, and chemotherapy. Triple-negative patients are especially responsive to platinum agents like cisplatin, carboplatin, oxaliplatin and satraplatin and taxanes including paclitaxel (Taxol) and docetaxel (Taxotere). Hormonal therapy and Herceptin are not indicated for triple-negative breast cancer. In addition new treatments that are being studied for triple-negative breast cancer can be used. A number of new strategies are currently being tested in clinical trials, including the PARP inhibitor BSI 201, NK012, and the targeted antibody-drug conjugate, Glembatumumab vedotin (CDX-011) (Anders C 2008. Oncology 22: 11).

Patients with HER2+ breast cancer are treated with Trastuzumab (Herceptin). which specifically targets HER2. Trastuzumab is often used with chemotherapy but it may also be used alone or in combination with hormone-blocking medications, such as an aromatase inhibitor or tamoxifen. HER2+ patients can also be treated with Lapatinib (Tykerb) in combination with the chemotherapy drug capecitabine (Xeloda) and the aromatase inhibitor letrozole (Femara). Lapatinib is also being studied in combination with trastuzumab. Further therapies may include an AKT inhibitor and/or an Tor inhibitor, either alone or in combination with hormone-blocking medication.

The invention further provides a method of typing a sample from a breast cancer patient according to the invention, the method further comprising classifying said sample as a ER+, triple negative, or HER2+; and assigning hormone therapy if the sample is classified as a ER+.

The female hormones oestrogen (ER) and progesterone (PR) can trigger the growth of some breast cancer cells. Therefore, ER+ patients are treated with drugs or treatments that lower the levels of oestrogen and progesterone or block their effects. There are three main types of hormone therapy. These are aromatase inhibitors, such as anastrozole, exemestane and letrozole, a drug called tamoxifen and treatment with luteinising hormone releasing hormone (LHRH) blockers such as goserilin (Zoladex) to stop the ovaries from working. Hormone therapy can be given before or after surgery, or to treat recurrent breast cancer. It is given alone or in combination with chemotherapy.

EXAMPLES

Example 1

Material and Methods
Patient Selection

A total of 1,212 patient specimens from 6 different studies were analyzed (an overview of the different cohorts used in this study can be found in Table 2). Cohort 1, described in van de Vijver et al. [van de Vijver et al. N Engl J Med 2002, 347:1999-2009], was used for the development (cohort 1a) and initial validation (cohort 1b) of the molecular subtyping profile. Cohort 1a samples (n=200) were selected for their concordance between classification based on their ER, PR and HER2 status by immunohistochemistry (IHC) and by TARGETPRINT(R) microarray based single gene readout (see below). Cohort 1b samples (n=95) had a discordance between IHC and TargetPrint ER, PR or HER2 determination. Cohort 2 consisted of 274 early-stage breast cancer samples from a consecutive series of patients seen at the Netherlands Cancer Institute and treated with adjuvant tamoxifen monotherapy [Kok et al. 2010 (submitted)]. Cohort 3 (n=100) was a group of patients from the RASTER trial [Bueno-de-Mesquita et al. Lancet Oncol 2007, 8(12): 1079-1087]. Additional validation of the profile was performed using two publicly available data sets: cohort 4, n=159 and cohort 5, n=251 (Table 2) [Pawitan et al. Breast Cancer Res 2005, 7(6):R953-964; Miller et al. Proc Natl Acad Sci USA 2005, 102:13550-13555]. The last cohort (cohort 6, Table 2), consisting of publicly available expression data from breast cancer patients (n=133), was used to determine the response to T/FAC neoadjuvant chemotherapy for patients sub-divided by molecular subtype [Hess et al. J Clin Oncol 2006, 24(26):4236-4244.3].

Microarray gene expression data

Pre-processed and normalized Agilent 22K dual-color expression data from cohort 1 was downloaded and duplicate dye-swap hybridizations were combined into a single log-ratio expression value per probe per sample. Samples from cohorts 2 and 3 were analyzed on Agilent arrays according to manufacturer's protocols. Expression data was quantified using Feature Extraction software. Pre-processed and normalized Affymetrix U133 A and U133 B gene expression data from cohorts 4 and 5 were available at the NCBI Gene Expression Omnibus (GEO) with accession numbers GSE1456(cohort 4) and GSE3494(cohort 5). Affymetrix data for cohort 6 was publicly available and downloaded. Microarray expression datasets were imported into R/Bioconductor software for further analysis. Affymetrix datasets were normalized by median scaling to represent the expression ratio distributions of cohorts 1-3.

ER, PR and HER2 Status by IHC and TargetPrint

The ER, PR and HER2 status of cohorts 1, 2, and 3 was determined by IHC and by TargetPrint (Agendia; see overview in Table 2) [McShane et al. J Clin Oncol. 2005 Dec. 20; 23(36):9067-72; Roepman et al. Clin Cancer Res 2009, 15(22):7004-70115]. Detailed procedures for centrally performed IHC and TargetPrint of the samples from cohorts 1-3 have been previously reported [Roepman et al. Clin Cancer Res 2009, 15(247004-70115]. As shown in Table 2, locally determined IHC status of ER was available for cohorts 5 and 6, PR status was available for cohort 5, and HER2 status was available for cohort 6. Receptor status of the publically available datasets was downloaded from their respective GEO websites.

Identification of an 80-Gene Molecular Subtyping Profile (BluePrint)

The 200 samples (cohort 1a) with concordant ER, PR and HER2 status were used for supervised training to identify gene expression profiles specific for three molecular subtyping classes: Triple-negative tumors, hormone receptor positive tumors and HER2-positive breast tumors. Using a 3-fold cross validation (CV) procedure, we identified the genes that best discriminate between the three molecular subtypes. Within each CV iteration, two-sample Welch t-tests were performed on a randomly selected set of 133 of the 200 training samples to score all genes for their differential expression among the three classes. Genes were ranked according to their absolute t-statistics and the 3-fold CV procedure was repeated a hundred times. Next, the 100 gene ranking scores were combined into a single ranking per gene and the minimal number of genes with optimal performance was determined using a leave-one-out CV on all 200 training samples. A good performance was achieved with a total of 80 unique genes (Table 3).

Next, a nearest-centroid classification model was built utilizing the 80-gene profile, in a fashion similar to that described previously [van 't Veer et al. Nature 2002, 415:530-536; Roepman et al. Clin Cancer Res 2009, 15(1):284-290; Glas et al. Blood. 2005, 105(1):301-307]. Cohort 1a was used to establish a Basal-type centroid profile (based on 28 genes), a Luminal-type profile (based on 58 genes) and a HER2-type profile (based on 4 genes). For all additional samples and for cohort 1a using a leave-one-out CV, a correlation index was calculated between the sample's 80-gene profile and each of the three MSP centroids.

Results

An 80-Gene Molecular Subtyping Profile

We used the TargetPrint assay [Roepman et al. Clin Cancer Res 2009, 15(22):7004-7011] to quantify ER, PR and HER2 mRNA levels in a training cohort of 295 breast cancer samples. We then used IHC/CISH to measure ER, PR and HER2 protein levels in the same 295 samples for the same three receptors. Employing the 200 samples with concordant ER, PR and HER2 status by IHC and TargetPrint mRNA readout (Table 2), a Molecular Subtyping Profile (MSP) was developed using a supervised training method. By using only concordant samples, we sought to capture ER, PR or HER2 regulated processes more reliably and robustly as compared to the use of each assay individually. Gene expression profiles were identified specific for three molecular subtypes: triple-negative tumors, hormone receptor-positive tumors and HER2-positive breast tumors. Using a 3-fold Cross Validation (CV) procedure, we identified 80 genes that best discriminated the three molecular subtypes (Table 3, FIG. 2A, see methods for details).

Testing of the profile on the 95 samples from cohort 1b (discordant for ER, PR and HER2 by IHC/CISH and TargetPrint, details in Table 2 and methods) showed that the Molecular Subtyping Profile was more concordant with the TargetPrint status than with ER, PR and HER2 status as determined by IHC. For example, of the nine IHC/CISH HER2-positive samples, only one was classified as MSP HER2-type, compared to all (7/7) of the TargetPrint HER2-positive samples. Similarly, only three of the seven IHC based triple-negative samples was classified as triple-negative by MSP, while eleven of the thirteen TargetPrint triple-negative samples showed a MSP triple-negative classification. Disease-free survival of patients in cohort 1 demonstrated a higher 5-year disease-free survival for patients with hormone receptor-positive tumors (77%, 95CI, 72-84%) compared to patients with HER2-positive (65%, 95CI: 53-81%) and triple-negative samples (64%, 95CI: 52-77%).

Confirmation of MSP in Independent Patient Cohorts

Next, classification of breast cancer samples into three molecular subtypes using the developed 80-gene MSP was performed using two independent patient cohorts with a total of 374 patient specimens (cohorts 2-3, Table 2). Of the 374 patients, 39 (10%) were classified as triple-negative, 263 (71%) were classified as hormone receptor-positive and 64 (19%) as HER2-positive (Table 2, FIG. 2b). Statistical analysis to validate the presence of the three MSP classes in the independent cohorts was performed using the in-group proportion (IGP) statistic, which is defined to be the proportion of samples in a group whose nearest neighbors are also in the same group, and can be considered as a measure of the robustness and reproducibility of the MSP profile in independent series [26]. The MSP classification of all three subtypes was highly preserved in cohorts 2 and 3, respectively, with an IGP of 0.98 and 0.88 for hormone receptor-positive, 0.87 and 0.94 for triple-negative and 0.78 and 0.89 for HER2-positive classifications (Table 4).

We also confirmed the MSP on microarray data generated by other investigators using Affymetrix arrays (cohort 4-5, Table 2). All 80 genes could be matched to the Affymetrix data using gene symbol or RefSeq annotation. Despite the use of different platforms and the fact that the data had been generated by other investigators, our in silico analysis shows similar MSP outcome distributions as observed in both the training and in-house independent cohorts with 73 out of 410 (18%) samples classified as triple-negative, 244 (60%) as hormone receptor-positive and 93 (23%) as HER2-positive (Table 2). Calculated IGP scores confirmed the reproducibility of the MSP classes on the two in-silico data sets (Table 4).

Comprehensive Breast Cancer Classification by MammaPrint and MSP

The 295 samples from cohort 1 have previously been stratified by risk of development of distant metastasis by MammaPrint [van de Vijver et al. N Engl J Med 2002, 347:1999-2009]. Here we have combined the MammaPrint based prognosis and the developed MSP to subtype the breast cancer samples into 4 groups: MammaPrint low-risk/ER+, MammaPrint high-risk/ER+, triple-negative and HER2-positive. The great majority (92%) of MammaPrint low-risk samples were ER+ by MSP, while the high-risk samples were more equally distributed across the MSP classes with 46% ER+, 26% triple-negative and 28% HER2-positive. The combined MammaPrint and MSP classification was confirmed in cohort 6 for which chemotherapy responsiveness data was available (see below). Eighty-six percent of the MammaPrint low-risk samples were ER+ compared to 53% of the MammaPrint high-risk samples.

Comparison of the 80-Gene Profile and the "Intrinsic Gene Set"

Molecular classification of breast cancer by the so-called "intrinsic gene set", as first identified by Perou et al., was based on hierarchical clustering without consideration of ER, PR and/or HER2-associated tumor biology [Perou et al. Nature 2000, 406:747-752]. In contrast, the MSP has been developed with ER, PR and HER2 status as a starting point. Direct comparison between the two methods is possible as cohort 1 samples have also been assessed using the "intrinsic gene set" (Table 5) [Fan et al. N Engl J Med 2006, 355(6): 560-569]. Despite the different strategies, classification by the MSP 80-gene profile is in agreement with classification based on the "intrinsic gene set" with an overall concordance of 92%. The "intrinsic gene set", Normal-like group was disregarded for this analysis since it is likely an artifact of having a high percentage of normal breast cells in the specimens of the original study [Parker et al. J Clin Oncol 2009, 27(8):1160-1167]. Agreement analysis with inclusion of the Normal-like class resulted in a concordance of 83%. Of note, within this analysis we underestimated the concordance with Perou classification as the MSP has no Normal-like counterpart and consequently all Normal-likes are discordant between both methods. The MSP classified 2 out of the twenty-nine "Normal-like samples" as triple-negative, 23 as hormone receptor-positive, and 4 as HER2-positive (Table 5). The concordance between MSP and the "intrinsic gene set" classification as mentioned above has been determined without sub-stratification into A and B subtypes of the ER+ and luminal-like classes. Comparison of the 165 ER+/luminal-like samples indicated that sub-stratification by MammaPrint or by Luminal A and B indicates a concordance of 74% between both methods (Table 5).

Chemotherapy Response

Publicly-available microarray expression data with full clinical history from a neo-adjuvant clinical study allowed in silico analysis of the 80-gene MSP as a predictor of pathological Complete Response (pCR) [Hess et al. J Clin Oncol 2006, 24(26):4236-4244]. MSP readout was determined on tumor samples from 133 breast cancer patients who were treated with neo-adjuvant T/FAC chemotherapy (cohort 6, Table 2). Within this cohort, 20% (n=27) were classified as triple-negative, 62% (n=82) as ER+, and 18% (n=24) as HER2+, with an IGP of 0.96 for triple-negative, 0.91 for ER+ and 0.75 for HER2+ (Table 4). The overall pCR of this patient cohort was 26% and differed substantially among the subgroups. PCR was observed in 9% of all ER+ samples and, importantly, only in 3% of MammaPrint low risk/ER+ and 11% in MammaPrint high risk/ER+, in 50% of the HER2+ samples and in 56% of the triple-negative samples.

Discussion

A Molecular Subtyping Profile (MSP) was identified that classifies breast cancer patients into triple negative, ER+ and HER2-type subgroups. The profile was developed in a supervised training method, using samples with concordant ER, PR and HER2 status by IHC and single-gene readout ensuring the capture of ER/PR/HER2-regulated processes and development of a more reliable and robust test than a single-gene read-out by IHC or mRNA measurement. The classification was validated on gene expression data from 917 samples in which the separation of the three subgroups was clearly maintained indicating the robustness of the profile and the reproducible differences among the subgroups. There is currently no "gold standard" for molecular subtyping of breast cancer. It is therefore unclear which method is best at classifying the ER+, HER2+ and triple-negative subtypes. For instance, although several investigators have used the term "triple negative" and "basal-like" interchangeably, it should be noted that these subtypes are not completely concordant and that additional markers are needed to separate them [Bertucci et al. Int J Cancer 2008, 123(1):236-240; Rakha et al. J Clin Oncol 2008, 26(15):2568-2581]. The MSP triple-negative subtype was developed with concordant negative IHC/TargetPrint-determined samples for ER, PR and HER2.

Pathological Complete Response (pCR) in the neoadjuvant setting can be used as a surrogate measure of response to chemotherapy and is associated with excellent long-term cancer-free survival [Fisher et al. J Clin Oncol 1998, 16(8):2672-2685; Kuerer et al. J Clin Oncol 1999, 17(2):460-469; Rastogi et al. J Clin Oncol 2008, 26(5):778-785]. We observed marked differences in response to neo-adjuvant treatment by molecular subtype as defined by the MSP, with a pCR of 3% in the MammaPrint low risk/ER+ samples, 11% in the MammaPrint high risk/ER+ samples, 50% in the HER2+ samples and 56% in the triple negative samples, in agreement with published data [Carey et al. Clin Cancer Res 2007, 13:2329-2334; Strayer et al. Breast Cancer Res Treat 2010, 119(3): 551-558]. These findings confirm differences in chemotherapy response between the subgroups, and are in agreement with the observation that ER+ samples are less responsive to chemotherapy than the other two molecular subgroups.

The notion that certain drugs are more effective in patients of particular subtypes has already led to clinical trials evaluating drug responses in molecularly-based subgroups. The outcome of these trials and future implementation of this knowledge may improve the clinical management of breast cancer patients by enabling the physician to decide who is most likely to benefit from which chemotherapy prior to surgery. Further, it may supplement information already available from validated multi-gene assays in helping the clinician decide on the best treatment for each patient. The MSP profile described here will help in the further establishment of a clinical correlation between molecular subtyping and treatment responses, especially in combination with MammaPrint; one biopsy sample is able to provide multiple answers.

Example 2

Molecular Subtyping Profile (MSP) can correctly classify subtypes with a minimal number of 2 genes from each subtype gene list: a random combination of 2 genes from the ER+ subtype gene list in Table 1A, a random combination of 2 genes from triple-negative subtype gene list in Table 1B and PERLD1 and SYCP3 from Her2 subtype gene list in Table 1C. A total of 200 random combinations were simulated. For each random combination, the assignments of molecular subtypes are compared with the assignment of molecular subtypes by an 80-genes molecular subtype profile listed in table 3. FIG. 1A shows the classification performances of 200 random combinations. Median consistency of 200 random combinations is 72.2%.

Figure 1B:
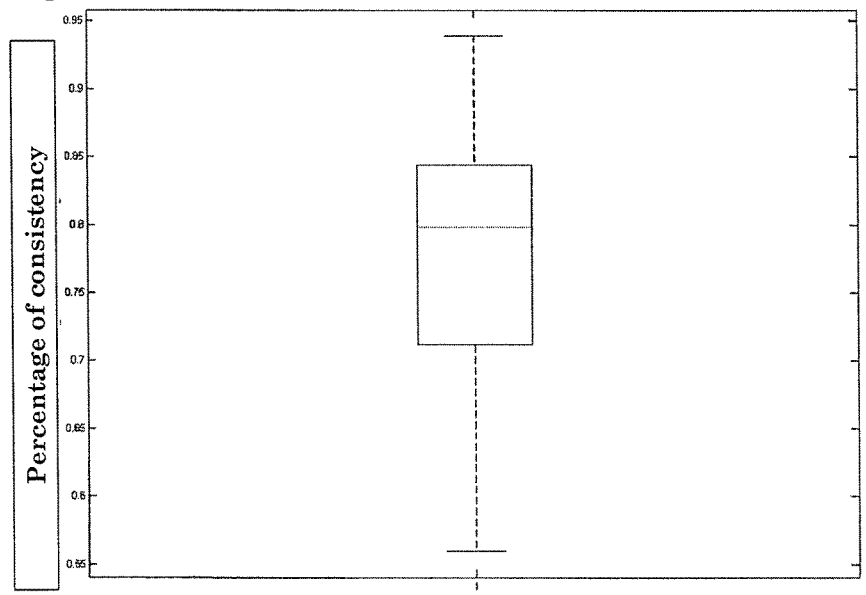

Molecular Subtyping Profile (MSP) can correctly classify subtypes with a minimal number of 3 genes from each subtype gene list: a random combination of 3 genes from ER+ subtype gene list in Table 1A, a random combination of 3 genes from triple-negative subtype gene list in Table 1B and all 3 genes from Her2 subtype gene list in Table 1C. Totally, 200 random combinations were simulated. For each random combination, the assignments of molecular subtypes are compared with the assignment of an 80-genes molecular subtype profile listed in Table 3. FIG. 1B shows the classification performances of 200 random combinations. Median consistency of 200 random combinations of three genes from Tables 1A-1C is 79.8%.

Example 3

Molecular Subtyping Profile (MSP) can be used to discriminate between triple negative, ER+ and HER2-type breast cancer. An ER+ type breast cancer is likely to have a functional estrogen receptor alpha. Conversely, a triple-negative type tumor would be expected to have a non-functional estrogen receptor alpha. One might therefore expect that breast tumors that are estrogen receptor alpha positive by immunohistochemistry (IHC), but triple negative by MSP-analysis, harbour a defective estrogen receptor.

To test this idea directly, we searched our patient database for patients that were ERalpha positive by IHC, but triple-negative type by MSP. We identified a patient (60 year old with 9 mm, moderately differentiated, HER2 negative, ER/PR>90% by IHC invasive ductal carcinoma) which had undergone both a MammaPrint(R), TargetPrint(R) and MSP test. She had MammaPrint high risk result. This patient was also ER-positive by TargetPrint, but triple-negative by MSP. This suggested that the ERalpha was present both at the protein and mRNA level, but non-functional.

We used the same RNA as was used to perform the TargetPrint and MSP test of this patient sample for detailed analysis of the estrogen receptor alpha in this patient. We first used reverse transcription to convert the mRNA of this tumor sample into cDNA and then used this cDNA to PCR amplify the coding sequence of estrogen receptor alpha with specific primers that span the start codon of ERalpha at the 5' end and the stop codon at the 3' end.

Agarose gelelectrophoresis of the PCR product revealed two distinct products: the expected full length open reading frame of ERalpha of 1785 base pairs and a second product of approximately 1500 base pairs (data not shown). The smaller PCR product was purified from the gel and subjected to DNA sequence analysis. Inspection of the DNA sequence revealed that this approximately 1500 base pair fragment encoded an ERalpha cDNA lacking exon 7 of the coding sequence (base pairs 1601-1785 relative to the transcription start site (see FIG. 1, from: Herynk and Fuqua. ER Mutations in human disease. Endocrine Reviews, 2004, 25(6):869-898)).

ERalpha cDNA lacking exon 7, termed ER E7, has been found to inhibit the function of the normal wild type estrogen receptor alpha in a dominant fashion (Garcia Pedrero et al. Endocrinology, 2003, 144:2967-2976). Thus the ER E7 is dominant negative for the normal ERalpha and inhibits its function. These data suggest that breast tumor cells that express the ER E7 variant of ERalpha have a severely attenuated transcriptional response of ERalpha in response to estradiol stimulation and hence these cells are functionally ER negative. Subsequently, we identified samples from an additional 10 patients that were ER+ by IHC but triple-negative by MSP. We were able to PCR amplify the estrogen receptor alpha cDNA from 6 out of these 10 patients using the approach described above. All 6 of these had a second PCR product of around 1500 base pairs, suggesting that all expressed the ER E7 variant.

We conclude that MSP measures functionality of the estrogen receptor and therefore detects functional ER status of patients beyond that identified by conventional IHC. The use of MSP is therefore a valuable tool to assess functional ER status in breast cancer, as patients that lack a functional ER are unlikely to respond to anti hormonal therapy.

TABLE 1A

Reporter genes for ER+ molecular subgroup

| SEQ ID NO | Accession number | Symbol | Sequence of probe | Up-down |
|---|---|---|---|---|
| 1 | NM_000060 | BTD | TCCTCTAACAAATCTCTCAGTATGCGATTGGTCTCAAGCTAAAACAAAAATAAATGTCAG | 0.99798 |
| 2 | NM_000191 | HMGCL | TCTCCACGCTGAATGTGATTTTTGAAAACAGCTTATGTAATTAAAGGTTGAATGGCACAT | 0.718379 |
| 3 | NM_000663 | ABAT | AAGTATGCTTTCTCCTGAAAACTTTAGCATTGGGTGCAAATATTCAGTATGGTTCTCGGA | 1.139217 |
| 4 | NM_000909 | NPY1R | TGTCCATCTTTCAAAGGAAGTAACACCAAGGTACAATGTTAAAGGAATATTCACTTTACC | 3.941573 |
| 5 | NM_001124 | ADM | GAAGGAAACACCGAGTCTCTGTATAATCTATTTACATAAAATGGGTGATATGCGAACAGC | -1.71619 |
| 6 | NM_001267 | CHAD | TCCATCTTCCCATGCTGCAATTTCTTCCTGAGATTTCTATAAATATAAATGTATGTATGT | 2.253163 |
| 7 | NM_001609 | ACADSB | CAGTGATTCTCAAGAAAAAGATCTCTTGCCCATTAAGAAGTGTATCAAAATCTCATAAGG | 1.348976 |
| 8 | NM_002115 | HK3 | CCCTGGCTTTCCCTGAGAGAAGTAGCACTCAGGTTAGCAATATATATATATAATTTATTT | -0.7687 |
| 9 | NM_002184 | IL6ST | TGAGGAAGATTTTGTTAGACTTAAACAGCAGATTTCAGATCATATTTCACAATCCTGTGG | 0.994592 |
| 10 | NM_003108 | SOX11 | CGTGTCTCAAGGTAGTTGCATACCTAGTCTGGAGTTGTGATTATTTTCCCAAAAAATGTG | -1.58459 |
| 11 | NM_003766 | BECN1 | GGTCTGAAATTTCAGAGATACCGACTTGTTCCTTACGGAAACCATTCATATCTGGAGTCT | 0.669302 |
| 12 | NM_003939 | BTRC | ATTTAACGTATCTGCCAATACCAGGATGAGCAACAACAGTAACAATCAAACTACTGCCCA | 1.121817 |
| 13 | NM_004358 | CDC25B | ATTTGTGTGGACAAAAATATTTACACTTAGGGTTTGGAGCTATTCAAGAGGAAATGTCAC | -1.18499 |
| 14 | NM_006864 | LILRB3 | TGTGGGACTCACCTGACTCAAAGATGACTAATATCGTCCCATTTTGGAAATAAAGCAACA | -1.09084 |
| 15 | NM_007083 | NUDT6 | TATTCATTCACCATAAATTTTTGCCAGGAAGAATGCTTAAGATGTGAGTGGATGGATCTC | 0.5761 |

TABLE 1A-continued

Reporter genes for ER+ molecular subgroup

| SEQ ID NO | Accession number | Symbol | Sequence of probe | Up-down |
|---|---|---|---|---|
| 16 | NM_014668 | GREB1 | GCACTCTAATGGATAACAATCCAAGAATAAATGATTGTAAAAGATGATGCCGAAGAGTTG | 2.171531 |
| 17 | NM_015130 | TBC1D9 | CTGGATGTTTAGCTTCTTACTGCAAAAACATAAGTAAAACAGTCAACTTTACCATTTCCG | 2.125057 |
| 18 | NM_016138 | COQ7 | AATGTGGGATCAAGAAAAGGACCATTTGAAAAAGTTCAATGAGTTGATGGTTATGTTCAG | 0.671002 |
| 19 | NM_017786 | GOLSYN | TTGCCGTTTTAAAATGTGTAATTGTTCCAGCATTCCAATGGTCTTGTGCATAGCAGGGGA | 1.430391 |
| 20 | NM_017830 | OCIAD1 | GCAAGGGCAAAGATAACTCTTAAAAAACCGTCGAGATTACAATGCTCTAGAATCAGCATA | 0.57447 |
| 21 | NM_018478 | DBNDD2 | GACAAGTGTCTCTAGATGGATGTGAACTCCTTAACTCATCAAGTAAGGTGGTACTCAAGC | 1.207345 |
| 22 | NM_020820 | PREX1 | TGTCTAACAGGGGACCAACAGAAGGTAGTATTGACAACTGTTCCCGCTTCTACTAAAAAA | 1.517446 |
| 23 | NM_024549 | TCTN1 | GACAATGCTCAGATGCATCAGTTCCTTAATATACACGTGAAATTTGAAAACTGTACATTC | 0.829769 |
| 24 | NM_024827 | HDAC11 | GGTCAGGAAGGGGTACAGGTGGGTTCCCTCATCTGGAGTTCCCCTCAATAAAGCAGGTCT | 0.727534 |
| 25 | NM_032376 | TMEM101 | AGGAAGATGGAGATTGGAAGTGAGCAAATGTGAAAAATTCCTCTTTGAACCTGGCAGATG | 1.002825 |
| 26 | NM_032521 | PARD6B | AAACACTGCCTACACTTTATGAAAACTACATAGTATTCACCTGTGACAGGTAGAGTTTAT | 1.690691 |
| 27 | NM_033426 | KIAA1737 | CTGTAAGTAGTGATGGTTTTAGCGATGAATAACGTAATTGGCTATGAAGTACTGTGGCAG | 0.885041 |
| 28 | NM_144686 | TMC4 | CATTGTAAGCCTAGGTCACAACATCTGTAAACTAGGAGAACTGGAGAAGACTCCACGCCC | 1.266353 |
| 29 | NM_145006 | SUSD3 | GGCCGTAACGATTTTTATAGTTATGGACTACTTGAAACCACTACTGAGGGTAATTTACTA | 2.624753 |
| 30 | NM_152376 | UBXD3 | AACACTTCCCAGAGAGGATTCTAGTCTGGTAAATAACCACAGTGTAGGAACTATCTAACT | 1.150527 |
| 31 | NM_153365 | TAPT1 | GAAAACTGTGAAACTTTTACCACGACGTAATCTTTCCAGTCTCATACTATTTTCACAAAC | 0.813243 |
| 32 | NM_173079 | RUNDC1 | GGGCAAATGTATCACTCCAAACACTACTGATTCAGCATTGTTTTCATGTCTTAAAATTG | 0.975909 |
| 33 | NM_203453 | PPAPDC2 | AAGCATAGATCATTTCACCTGATGTTTTTGAAGCATCCTAAGTACAGTAGAGTAGAAAAC | 0.773664 |
| 34 | NM_207310 | CCDC74B | TTCTAGCTGTTATTTTGCTATTTGGCATTTACATAAAAGCACACGATGAAGCAGGTATCG | 2.412199 |
| 35 | NM198485 | TPRG1 | TGCCCGTGGGAGTATTGGTTTTTGAGAGTCTTTTTGGTACCATAAGCATATCATCCACAG | 2.962995 |

TABLE 1B

Reporter genes for triple-negative molecular subgroup

| SEQ ID NO | Accession number | Symbol | Sequence of probe | Up-down |
|---|---|---|---|---|
| 36 | NM_001267 | CHAD | TCCATCTTCCCATGCTGCAATTTCTTCCTGAGATTTCTATAAATATAAATGTATGTATGT | -2.4616 |
| 37 | NM_001609 | ACADSB | CAGTGATTCTCAAGAAAAAGATCTCTTGCCCATTAAGAAGTGTATCAAAATCTCATAAGG | -1.48367 |
| 38 | NM_002444 | MSN | GCATTGCTGTGAATTAGCTCACTTGGTGATATGTCCTATATTGGCTAAATTGAAACCTGG | 1.200003 |
| 39 | NM_005794 | DHRS2 | CTTCAGCAAAGTGTTTCATGGGAATGAGTCTCTCTGGAAGAACTTCAAGGAACATCATCA | -2.68104 |
| 40 | NM_014668 | GREB1 | GCACTCTAATGGATAACAATCCAAGAATAAATGATTGTAAAAGATGATGCCGAAGAGTTG | -2.50524 |
| 41 | NM_015130 | TBC1D9 | CTGGATGTTTAGCTTCTTACTGCAAAAACATAAGTAAAACAGTCAACTTTACCATTTCCG | -2.62505 |
| 42 | NM_015417 | SPEF1 | AAGGTTTGAAGGTTACGGCTCAGGGCTGCCCCATTAAAGTCAGTGTTGTGTTCTAAAAAA | -1.41448 |
| 43 | NM_024817 | THSD4 | TATTACATAAGCAGGTGAAAGGTAGAAGGCGAATTATGTGAGTAAATATGGTCTGTTTTC | -2.49307 |
| 44 | NM_033419 | PERLD1 | GAAAACTTTTAAGGTGGGAGGGTGGCAAGGGATGTGCTTAATAAATCAATTCCAAGCCTC | -2.15998 |
| 45 | NM_145186 | ABCC11 | CATCTAAGACATGGGATTCAGTGATCATGTGGTTCTCCTTTTAACTTACATGCTGAATAA | -3.08474 |
| 46 | NM_175887 | PRR15 | ATGTTAAACTACAAAACTGTACAGCCTATTTTAGTGTGGACTATTAAAACCCTTGCACTG | -3.46006 |

TABLE 1B-continued

Reporter genes for triple-negative molecular subgroup

| SEQ ID NO | Accession number | Symbol | Sequence of probe | Up-down |
|---|---|---|---|---|
| 47 | NM_177433 | MAGED2 | GCTATTCCTTGGAGAAGGTATTTGGGATTCAATTGAAGGAAATTGATAAGAATGACCACT | -1.66856 |
| 48 | NM_178568 | RTN4RL1 | GGGGAACAATGAGGGCATTTCATGAACCATCTCAGGCACTTCTGCATCACGGAAGACCTG | -0.86324 |

TABLE 1C

Reporter genes for HER2 molecular subgroup

| SEQ ID NO | Acc | Symbol | Sequence of probe | Up-down |
|---|---|---|---|---|
| 49 | NM_033419 | PERLD1 | GAAAACTTTTAAGGTGGGAGGGTGGCAAGGGATGTGCTTAATAAATCAATTCCAAGCCTC | 2.959689 |
| 50 | NM_153694 | SYCP3 | TTCTTTCTTCAAAGAGTCATCAGAATAACATGGATTGAAGAGACTTCCGAACACTTGCTA | -1.17653 |
| 51 | NM_004448 | ERBB2 | GAAGGAACAGCAATGGTGTCAGTATCCAGGCTTTGTACAGAGTGCTTTTCTGTTTAGTTT | 3.631029 |

TABLE 2

Overview and characteristics of the training and validation cohorts

| | Cohorts # | | | | | |
|---|---|---|---|---|---|---|
| | 1* | 2 | 3** | 4 | 5 | 6 |
| samples (n) | 295 | 274 | 100 | 159 | 951 | 133 |
| Array | Agilent 22k | Agilent 44K | Agilent 44K | Affymetrix U133 | Affymetrix U133 | Affymetrix U133 |
| Subsets* | 1a 1b | | | | | |
| Samples (n) | 200 95 | | | | | |
| Purpose | training validation | independent validation | independent validation | in silico validation | in silico validation | in silico validation chemo-response |
| *MSP class* | | | | | | |
| ER+ | 60% 74% | 78% | 49% | 67% | 60% | 62% |
| Triple-negative | 16% 16% | 8% | 16% | 17% | 30% | 20% |
| HER2+ | 24% 11% | 14% | 35% | 16% | 10% | 18% |
| *TargetPrint* | | | | | | |
| ER positive | 77% 80% | 80% | 71% | | | |
| PR positive | 72% 43% | 47% | 61% | na | na | na |
| HER2 positive | 24% 7% | 13% | 39% | | | |
| *IHC (+CISH for HER2)* | | | | | | |
| ER positive | 73% 78% | 84% | 68% | | 85% | 62% |
| PR positive | 72% 49% | 46% | 49% | na | 76% | na |
| HER2 positive | 24% 13% | 13% | 38% | | na | 25% |

*Cohort 1 was divided into training cohort 1a that consisted of samples with concordant TargetPrint and IHC based receptor classification, and into validation cohort 1b that consisted of samples that were discordant between IHC and TargetPrint based classification.
**Samples within cohort 3 have been selected to include approximately two-thirds hormone positive samples and one-third HER2 positive samples.
Note:
not all percentages sum to 100 because of rounding

TABLE 3

Overview of reporter genes for Triple-negative, ER+ and HER2 molecular subgroups

| ER+ | | | | Triple-negative | | HER2 | |
|---|---|---|---|---|---|---|---|
| NM_000663 | ABAT | NM_006864 | LILRB3 | NM_145186 | ASCC11 | NM_004448 | ERBB2 |
| NM_001609 | ACADSB | NM_015541 | LRIG1 | NM_001609 | ACADSB | NM_001030002 | GRB7 |
| NM_024722 | ACBD4 | NM_005375 | MYB | NM_002286 | AFF3 | NM_033419 | PERLD1 |
| NM_001124 | ADM | NM_000662 | NAT1 | NM_006408 | AGR2 | NM_153694 | SYCP3 |
| NM_002285 | AFF3 | NM_000909 | NPY1R | NM_000044 | AR | | |
| NM_000633 | BCL2 | NM_007083 | NUDT6 | NM_206925 | CA12 | | |
| NM_003766 | BECN1 | NM_017830 | OCIAD1 | NM_144575 | CAPN13 | | |
| NM_000060 | BTD | NM_032521 | PARD6B | NM_031942 | CDCA7 | | |
| NM_003939 | BTRC | NM_000926 | PGR | NM_001267 | CHAD | | |
| NM_206925 | CA12 | NM_203453 | PPAPDC2 | NM_005794 | DHRS2 | | |
| NM_207310 | CCDC74B | NM_020820 | PREX1 | NM_000125 | EGR1 | | |
| NM_004358 | CDC2SB | NM_032918 | RERG | NM_004496 | FOXA1 | | |
| NM_014246 | CELSR1 | NM_173079 | RUNDC1 | NM_001453 | FOXC1 | | |
| NM_001408 | CELSR2 | NM_002964 | SI00A8 | NM_001002295 | GATA3 | | |
| NM_001267 | CHAD | NM_020974 | SCUBE2 | NM_014668 | GREB1 | | |
| NM_016138 | COQ7 | NM_003108 | SOX11 | NM_019600 | KIAA1370 | | |
| NM_003462 | DNALM | NM_145006 | SUSO3 | NM_177433 | MAGED2 | | |
| NM_021814 | ELOVL5 | NM_153365 | TAPT1 | NM_024101 | MLPH | | |
| NM_000125 | ESR1 | NM_015130 | TBC1D9 | NM_020444 | MSM | | |
| NM_001002295 | GATA3 | NM_024549 | TCTN1 | NM_018728 | MYOSC | | |
| NM_017786 | GOLSYN | NM_024817 | THSO4 | NM_033419 | PERLD1 | | |
| NM_014668 | GREB1 | NM_144686 | TMC4 | NM_175887 | PRR15 | | |
| NM_024827 | HOAC11 | NM_032376 | TMEM101 | NM_138393 | REEP6 | | |
| NM_002115 | HX3 | NM_021103 | TMSB10 | NM_178568 | RTN4RL1 | | |
| NM_000191 | HMGCL | NM_198485 | TPRG1 | NM_004694 | GLC16A6 | | |
| NM_002184 | IL627 | NM_152376 | UBXD3 | NM_015417 | SPEF1 | | |
| NM_005544 | YRS1 | NM_018478 | OBNDD2 | NM_015130 | TBC1D9 | | |
| NM_033426 | KIAA1737 | NM_006113 | VAV3 | NM_024817 | THSD4 | | |
| NM_006733 | KIF20A | NM_005080 | XEP1 | | | | |

TABLE 4

In group proportion statistics (IGP) for the MSP classes across the independent cohorts

| | | In-group proportion (IGP)* | | | | |
|---|---|---|---|---|---|---|
| | | Cohort 2 | Cohort 3 | Cohort 4 | Cohort 5 | Cohort 6 |
| MSP class | ER+ (Luminal-like) | 0.98 | 0.88 | 0.92 | 0.91 | 0.91 |
| | Triple-negative (Basal-like) | 0.87 | 0.94 | 0.92 | 0.68 | 0.96 |
| | HER2-positive | 0.78 | 0.89 | 0.56 | 0.68 | 0.75 |

*IGP is defined as the proportion of samples in a group whose nearest neighbours are also in the same group and can be considered as a measurement for the robustness and reproducibility of identified cluster/classes across independent data sets [28]. Note: an ideal cohort has an IGP value of 1.0.

TABLE 6

Overview of additional reporter genes for HER2 molecular subgroup

| NM_002809 | PSMD3 | >95% | positive |
|---|---|---|---|
| NM_003673 | TCAP | >95% | positive |
| NM_004774 | MED1 | >95% | positive |
| NM_016507 | CDK12 | >95% | positive |
| NM_002686 | PNMT | >95% | positive |
| NM_018530 | GSDMB | >95% | positive |
| NM_032875 | FBXL20 | >90% | positive |
| NM_000981 | RPL19P12 | >80% | positive |
| NM_198477 | CXCL17 | >80% | positive |
| NM_002795 | PSMB3 | >50% | positive |
| NM_018478 | DBNDD2 | >95% | negative |
| NM_003559 | PIP4K2B | >60% | positive |
| NM_024306 | FA2H | >80% | positive |
| NM_000888 | ITGB6 | >90% | positive |
| NM_000402 | G6PD | >95% | positive |
| NM_006148 | LASP1 | >80% | positive |
| NM_002859 | PXN | >95% | positive |
| NM_145186 | ABCC11 | >95% | positive |

TABLE 5

Comparison of MSP with classification using the "intrinsic gene set" on cohort 1
Clustering of patients by "intrinsic gene set"

| | | Luminal A | Luminal B | Basal-like | Her2-like | "Normal-like" | Total |
|---|---|---|---|---|---|---|---|
| Molecular subtyping by MSP | Low-risk MammaPrint ER+ | 83 | 9 | 0 | 0 | 14 | 106 |
| | High-risk MammaPrint ER+ | 34 | 39 | 2 | 0 | 9 | 84 |
| | Triple-negative | 0 | 0 | 44 | 0 | 2 | 46 |
| | HER2 | 6 | 7 | 7 | 35 | 4 | 59 |
| | Total | 123 | 55 | 53 | 35 | 29 | 295 |

TABLE 6-continued

Overview of additional reporter genes for HER2 molecular subgroup

| | | | |
|---|---|---|---|
| NM_021202 | TP53INP2 | >90% | positive |
| NM_152463 | EME1 | >60% | positive |
| NM_002714 | PPP1R10 | >80% | positive |
| NM_178031 | TMEM132A | >95% | positive |
| NM_001007075 | KLHL5 | >95% | negative |
| NM_007144 | PCGF2 | >60% | positive |
| NM_178177 | NMNAT3 | >70% | negative |
| NM_002168 | IDH2 | >60% | positive |
| NM_006536 | CLCA2 | >60% | positive |
| NM_017957 | EPN3 | >95% | positive |
| NM_030938 | TMEM49 | >60% | positive |
| NM_198581 | ZC3H6 | >80% | negative |
| NM_000855 | GUCY1A2 | >80% | positive |
| NM_006262 | PRPH | >80% | positive |
| NM_030630 | C17orf28 | >95% | positive |
| NM_018219 | CCDC87 | >80% | positive |
| NM_018964 | SLC37A1 | >60% | positive |
| NM_021127 | PMAIP1 | >90% | negative |
| NM_000695 | ALDH3B2 | >90% | positive |
| NM_138788 | TMEM45B | >95% | positive |
| NM_013257 | SGK3 | >90% | negative |
| NM_014851 | KLHL21 | >95% | negative |
| NM_001017526 | ARHGAP8 | >95% | positive |
| NM_001014432 | AKT1 | >80% | positive |
| NM_007212 | RNF2 | >70% | negative |
| NM_014553 | TFCP2L1 | >95% | negative |
| NM_000637 | GSR | >90% | positive |

The invention claimed is:

1. A method of assigning treatment to a patient suffering from breast cancer, comprising
   (a) typing a sample from the patient according to a method comprising:
   determining a level of RNA expression for ADM and CCDC74B, and, optionally for at least one gene selected from the group consisting of: BTD, HMGCL, ABAT, NPY1R, CHAD, ACADSB, HK3, IL6ST, SOX11, BECN1, BTRC, CDC25B, LILRB3, NUDT6, GREB1, TBC1D9, COQ7, GOLSYN, OCIAD1, DBNDD2, PREX1, TCTN1, HDAC11, TMEM101, PARD6B, KIAA1737, TMC4, SUSD3, UBXD3, TAPT1, RUNDC1, PPAPDC2, and TPRG1; and
   determining a level of RNA expression for MSN and THSD4 and, optionally for at least one gene selected from the group consisting of: CHAD, ACADSB, DHRS2, GREB1, TBC1D9, SPEF1, PERLD1, ABCC11, PRR15, MAGED2, RTN4RL1; and
   determining a level of RNA expression for PERLD1 and SYCP3 and optionally for ERBB2,
   in the sample from the patient by microarray analysis with probes having SEQ ID NOs: 5, 34, 38, 43, 49 and 50,
   whereby the sample from the patient comprises RNA expression products from a breast cancer cell of the patient, said breast cancer cell being obtained from the patient during or after surgery and/or biopsy;
   converting said RNA expression products into a labelled sample comprising either complementary DNA (cDNA) or cRNA with a reverse-transcriptase enzyme and labelled nucleotides,
   hybridizing the labelled sample against the probes that are spotted on an array,
   washing the array to remove labelled sample that did not hybridize,
   analyzing amount of labelled sample that remains on the array to determine a level of RNA expression of the at least six genes,
   comparing said determined level of RNA expression of the at least six genes to the level of expression of the genes in a reference sample which reference sample comprises RNA expression products from breast cells; and
   typing said sample from the patient based on the comparison of the determined levels of RNA expression, whereby downregulation of ADM and upregulation of CCDC74B in the sample from the patient, when compared to the reference sample, is indicative of ER+, downregulation of THSD4 and upregulation of MSN in the sample from the patient, when compared to the reference sample, is indicative of triple negative, and downregulation of SYCP3 and upregulation of PERLD1 in the sample from the patient, when compared to the reference sample, is indicative of HER2;
   (b) classifying said sample from the patient as a ER+, triple negative, or HER2+;
   (c) assigning treatment comprising a platinum agent and/or a taxane to an individual of which the sample from the patient is classified as triple negative and, assigning treatment comprising trastuzumab, lapatinib, an aromatase inhibitor and/or Tamoxifen to an individual of which the sample from the patient is classified as HER2+.

2. The method according to claim 1, whereby at least one further gene is selected from SOX11, CDC25B and LILRB3 which are downregulated in an ER+ breast cancer, compared to the level of expression in the reference sample.

3. The method according to claim 1, whereby at least one further gene is selected from PRR15, ABCC11, DHRS2, TBC1D9, GREB1, PERLD1, MAGED2, ACADSB, SPEF1, CHAD, and RTN4RL1 which are downregulated in a triple-negative breast cancer, compared to the level of expression in the reference sample.

4. The method according to claim 1, whereby a level of RNA expression of at least three further genes from BTD, HMGCL, ABAT, NPY1R, CHAD, ACADSB, HK3, IL6ST, SOX11, BECN1, BTRC, CDC25B, LILRB3, NUDT6, GREB1, TBC1D9, COQ7, GOLSYN, OCIAD1, DBNDD2, PREX1, TCTN1, HDAC11, TMEM101, PARD6B, KIAA1737, TMC4, SUSD3, UBXD3, TAPT1, RUNDC1, PPAPDC2, and TPRG1 is determined.

5. The method according to claim 1, further comprising determining a metastasizing potential of the sample from the patient.

6. The method according to claim 5, whereby the metastasizing potential is determined by a 70 gene profile.

7. The method according to claim 1, whereby at least one further gene is selected from TMEM101, BTRC, ABAT, UBXD3, DBNDD2, TMC4, ACADSB, GOLSYN, PREX1, PARD6B, TBC1D9, GREB1, CHAD, SUSD3, TPRG1, NPY1R, OCIAD1, NUDT6, BECN1, COQ7, HMGCL, HDAC11, HK3, PPAPDC2, TAPT1, TCTN1, KIAA1737, RUNDC1, IL6ST, and BTD, which are upregulated in a ER+ breast cancer, compared to the level of expression in the reference sample.

8. A method of assigning treatment to a patient suffering from breast cancer, comprising
   (a) typing a sample from the patient according to a method comprising:
   determining a level of RNA expression for ADM and CCDC74B, and, optionally for at least one gene selected from the group consisting of: BTD, HMGCL, ABAT, NPY1R, CHAD, ACADSB, HK3, IL6ST, SOX11, BECN1, BTRC, CDC25B, LILRB3, NUDT6, GREB1, TBC1D9, COQ7, GOLSYN, OCIAD1, DBNDD2, PREX1, TCTN1, HDAC11, TMEM101, PARD6B, KIAA1737, TMC4, SUSD3, UBXD3, TAPT1, RUNDC1, PPAPDC2, and TPRG1; and determining a level of RNA expression for MSN and THSD4, and, optionally for at least one gene selected from the group consisting of: CHAD, ACADSB, DHRS2, GREB1, TBC1D9, SPEF1, PERLD1, ABCC11, PRR15, MAGED2, RTN4RL1; and determining a level of RNA expression for PERLD1 and SYCP3, and optionally for ERBB2, in the sample from the patient, by microarray analysis with probes having SEQ ID NOs: 5, 34, 38, 43, 49 and 50, whereby the sample from the patient comprises RNA expression products from a breast cancer cell of the patient, said breast cancer cell being obtained from the patient during or after surgery and/or biopsy;

converting said RNA expression products into a labelled sample comprising either complementary DNA (cDNA) or cRNA with a reverse-transcriptase enzyme and labelled nucleotides, hybridizing the labelled sample against the probes that are spotted on an array, washing the array to remove labelled sample that did not hybridize, analyzing the amount of labelled sample that remains on the array to determine a level of RNA expression of the at least six genes, comparing said determined level of RNA expression of the at least six genes to the level of expression of the genes in a reference sample which reference sample comprises RNA expression products from breast cells; and typing said sample from the patient based on the comparison of the determined levels of RNA expression, whereby downregulation of ADM and upregulation of CCDC74B in the sample from the patient, when compared to the reference sample, is indicative of ER+, downregulation of THSD4 and upregulation of MSN in the sample from the patient, when compared to the reference sample, is indicative of triple negative, and downregulation of SYCP3 and upregulation of PERLD1 in the sample from the patient, when compared to the reference sample, is indicative of HER2;

(b) classifying said sample as a ER+, triple negative, or HER2+;

(c) assigning hormone therapy comprising an aromatase inhibitor, Tamoxifen and/or a lutenizing hormone releasing hormone (LHRH) blocker to an individual if the sample is classified as a ER+.

9. The method according to claim 8, whereby at least one further gene is selected from SOX11, CDC25B and LILRB3, which are downregulated in a ER+ breast cancer, compared to the level of expression in the reference sample.

10. The method according to claim 8, whereby at least one further gene is selected from PRR15, ABCC11, DHRS2, TBC1D9, GREB1, PERLD1, MAGED2, ACADSB, SPEF1, CHAD, and RTN4RL1, which are downregulated in a triple-negative breast cancer, compared to the level of expression in the reference sample.

11. The method according to claim 8, whereby a level of RNA expression of at least five genes from SEQ ID NOs: 1-35 is determined.

12. The method according to claim 8, further comprising determining a metastasizing potential of the sample from the patient.

13. The method according to claim 12, whereby the metastasizing potential is determined by a 70 gene profile.

14. The method according to claim 8, whereby at least one further gene is selected from TMEM101, BTRC, ABAT, UBXD3, DBNDD2, TMC4, ACADSB, GOLSYN, PREX1, PARD6B, TBC1D9, GREB1, CHAD, SUSD3, TPRG1, NPY1R OCIAD1, NUDT6, BECN1, COQ7, HMGCL, HDAC11, HK3, PPAPDC2, TAPT1, TCTN1, KIAA1737, RUNDC1, IL6ST, and BTD, which are upregulated in a triple negative breast cancer, compared to the level of expression in the reference sample.

* * * * *

SEQUENCE LISTING

<160> NUMBER OF SEQ ID NOS: 51

<210> SEQ ID NO 1
<211> LENGTH: 60
<212> TYPE: DNA
<213> ORGANISM: Artificial
<220> FEATURE:
<223> OTHER INFORMATION: NM_000060

<400> SEQUENCE: 1
tcctctaaca aatctctcag tatgcgattg gtctcaagct aaaacaaaaa taaatgtcag    60

<210> SEQ ID NO 2
<211> LENGTH: 60
<212> TYPE: DNA
<213> ORGANISM: Artificial
<220> FEATURE:
<223> OTHER INFORMATION: NM_000191

<400> SEQUENCE: 2
tctccacgct gaatgtgatt tttgaaaaca gcttatgtaa ttaaaggttg aatggcacat    60

<210> SEQ ID NO 3
<211> LENGTH: 60
<212> TYPE: DNA
<213> ORGANISM: Artificial
<220> FEATURE:
<223> OTHER INFORMATION: NM_000663

<400> SEQUENCE: 3
aagtatgctt tctcctgaaa actttagcat tgggtgcaaa tattcagtat ggttctcgga    60

<210> SEQ ID NO 4
<211> LENGTH: 60
<212> TYPE: DNA
<213> ORGANISM: Artificial
<220> FEATURE:
<223> OTHER INFORMATION: NM_000909

<400> SEQUENCE: 4
tgtccatctt tcaaaggaag taacaccaag gtacaatgtt aaaggaatat tcactttacc    60

<210> SEQ ID NO 5
<211> LENGTH: 60
<212> TYPE: DNA
<213> ORGANISM: Artificial
<220> FEATURE:
<223> OTHER INFORMATION: NM_001124

<400> SEQUENCE: 5
gaaggaaaca ccgagtctct gtataatcta tttacataaa atgggtgata tgcgaacagc    60

<210> SEQ ID NO 6
<211> LENGTH: 60
<212> TYPE: DNA
<213> ORGANISM: Artificial
<220> FEATURE:
<223> OTHER INFORMATION: NM_001267

<400> SEQUENCE: 6
tccatcttcc catgctgcaa tttcttcctg agatttctat aaatataaat gtatgtatgt    60

<210> SEQ ID NO 7
<211> LENGTH: 60
<212> TYPE: DNA
<213> ORGANISM: Artificial
<220> FEATURE:
<223> OTHER INFORMATION: NM_001609

<400> SEQUENCE: 7
cagtgattct caagaaaaag atctcttgcc cattaagaag tgtatcaaaa tctcataagg    60

<210> SEQ ID NO 8
<211> LENGTH: 60
<212> TYPE: DNA
<213> ORGANISM: Artificial
<220> FEATURE:
<223> OTHER INFORMATION: NM_002115

<400> SEQUENCE: 8
ccctggcttt ccctgagaga agtagcactc aggttagcaa tatatatata taatttattt    60

<210> SEQ ID NO 9
<211> LENGTH: 60
<212> TYPE: DNA
<213> ORGANISM: Artificial
<220> FEATURE:
<223> OTHER INFORMATION: NM_002184

<400> SEQUENCE: 9
tgaggaagat tttgttagac ttaaacagca gatttcagat catatttcac aatcctgtgg    60

<210> SEQ ID NO 10
<211> LENGTH: 60
<212> TYPE: DNA
<213> ORGANISM: Artificial
<220> FEATURE:
<223> OTHER INFORMATION: NM_003108

<400> SEQUENCE: 10
cgtgtctcaa ggtagttgca tacctagtct ggagttgtga ttattttccc aaaaaatgtg    60

<210> SEQ ID NO 11
<211> LENGTH: 60
<212> TYPE: DNA
<213> ORGANISM: Artificial
<220> FEATURE:
<223> OTHER INFORMATION: NM_003766

<400> SEQUENCE: 11
ggtctgaaat ttcagagata ccgacttgtt ccttacggaa accattcata tctggagtct    60

<210> SEQ ID NO 12
<211> LENGTH: 60
<212> TYPE: DNA
<213> ORGANISM: Artificial
<220> FEATURE:
<223> OTHER INFORMATION: NM_003939

<400> SEQUENCE: 12
atttaacgta tctgccaata ccaggatgag caacaacagt aacaatcaaa ctactgccca    60

<210> SEQ ID NO 13
<211> LENGTH: 60
<212> TYPE: DNA
<213> ORGANISM: Artificial
<220> FEATURE:
<223> OTHER INFORMATION: NM_004358

<400> SEQUENCE: 13
atttgtgtgg acaaaaatat ttacacttag ggtttggagc tattcaagag gaaatgtcac    60

<210> SEQ ID NO 14
<211> LENGTH: 60
<212> TYPE: DNA
<213> ORGANISM: Artificial
<220> FEATURE:
<223> OTHER INFORMATION: NM_006864

<400> SEQUENCE: 14
tgtgggactc acctgactca aagatgacta atatcgtccc attttggaaa taaagcaaca    60

<210> SEQ ID NO 15
<211> LENGTH: 60
<212> TYPE: DNA
<213> ORGANISM: Artificial
<220> FEATURE:
<223> OTHER INFORMATION: NM_007083

<400> SEQUENCE: 15
tattcattca ccataaattt ttgccaggaa gaatgcttaa gatgtgagtg gatggatctc    60

<210> SEQ ID NO 16
<211> LENGTH: 60
<212> TYPE: DNA
<213> ORGANISM: Artificial
<220> FEATURE:
<223> OTHER INFORMATION: NM_014668

<400> SEQUENCE: 16
gcactctaat ggataacaat ccaagaataa atgattgtaa aagatgatgc cgaagagttg    60

<210> SEQ ID NO 17
<211> LENGTH: 60
<212> TYPE: DNA
<213> ORGANISM: Artificial
<220> FEATURE:
<223> OTHER INFORMATION: NM_015130

<400> SEQUENCE: 17
ctggatgttt agcttcttac tgcaaaaaca taagtaaaac agtcaacttt accatttccg    60

<210> SEQ ID NO 18
<211> LENGTH: 60
<212> TYPE: DNA
<213> ORGANISM: Artificial
<220> FEATURE:
<223> OTHER INFORMATION: NM_016138

<400> SEQUENCE: 18
aatgtgggat caagaaaagg accatttgaa aaagttcaat gagttgatgg ttatgttcag    60

<210> SEQ ID NO 19
<211> LENGTH: 60
<212> TYPE: DNA
<213> ORGANISM: Artificial
<220> FEATURE:
<223> OTHER INFORMATION: NM_017786

<400> SEQUENCE: 19
ttgccgtttt aaaatgtgta attgttccag cattccaatg gtcttgtgca tagcagggga    60

<210> SEQ ID NO 20
<211> LENGTH: 60
<212> TYPE: DNA
<213> ORGANISM: Artificial
<220> FEATURE:
<223> OTHER INFORMATION: NM_017830

<400> SEQUENCE: 20
gcaagggcaa agataactct taaaaaaccg tcgagattac aatgctctag aatcagcata    60

<210> SEQ ID NO 21
<211> LENGTH: 60
<212> TYPE: DNA
<213> ORGANISM: Artificial
<220> FEATURE:
<223> OTHER INFORMATION: NM_018478

<400> SEQUENCE: 21
gacaagtgtc tctagatgga tgtgaactcc ttaactcatc aagtaaggtg gtactcaagc    60

<210> SEQ ID NO 22
<211> LENGTH: 60
<212> TYPE: DNA
<213> ORGANISM: Artificial
<220> FEATURE:
<223> OTHER INFORMATION: NM_020820

<400> SEQUENCE: 22
tgtctaacag gggaccaaca gaaggtagta ttgacaactg ttcccgcttc tactaaaaaa    60

<210> SEQ ID NO 23
<211> LENGTH: 60
<212> TYPE: DNA
<213> ORGANISM: Artificial
<220> FEATURE:
<223> OTHER INFORMATION: NM_024549

<400> SEQUENCE: 23
gacaatgctc agatgcatca gttccttaat atacacgtga aatttgaaaa ctgtacattc    60

<210> SEQ ID NO 24
<211> LENGTH: 60
<212> TYPE: DNA
<213> ORGANISM: Artificial
<220> FEATURE:
<223> OTHER INFORMATION: NM_024827

<400> SEQUENCE: 24
ggtcaggaag gggtacaggt gggttccctc atctggagtt cccctcaata aagcaggtct    60

```
<210> SEQ ID NO 25
<211> LENGTH: 60
<212> TYPE: DNA
<213> ORGANISM: Artificial
<220> FEATURE:
<223> OTHER INFORMATION: NM_032376

<400> SEQUENCE: 25
aggaagatgg agattggaag tgagcaaatg tgaaaaattc ctctttgaac ctggcagatg    60

<210> SEQ ID NO 26
<211> LENGTH: 60
<212> TYPE: DNA
<213> ORGANISM: Artificial
<220> FEATURE:
<223> OTHER INFORMATION: NM_032521

<400> SEQUENCE: 26
aaacactgcc tacactttat gaaaactaca tagtattcac ctgtgacagg tagagtttat    60

<210> SEQ ID NO 27
<211> LENGTH: 60
<212> TYPE: DNA
<213> ORGANISM: Artificial
<220> FEATURE:
<223> OTHER INFORMATION: NM_033426

<400> SEQUENCE: 27
ctgtaagtag tgatggtttt agcgatgaat aacgtaattg gctatgaagt actgtggcag    60

<210> SEQ ID NO 28
<211> LENGTH: 60
<212> TYPE: DNA
<213> ORGANISM: Artificial
<220> FEATURE:
<223> OTHER INFORMATION: NM_144686

<400> SEQUENCE: 28
cattgtaagc ctaggtcaca acatctgtaa actaggagaa ctggagaaga ctccacgccc    60

<210> SEQ ID NO 29
<211> LENGTH: 60
<212> TYPE: DNA
<213> ORGANISM: Artificial
<220> FEATURE:
<223> OTHER INFORMATION: NM_145006

<400> SEQUENCE: 29
ggccgtaacg attttttatag ttatggacta cttgaaacca ctactgaggg taatttacta   60

<210> SEQ ID NO 30
<211> LENGTH: 60
<212> TYPE: DNA
<213> ORGANISM: Artificial
<220> FEATURE:
<223> OTHER INFORMATION: NM_152376

<400> SEQUENCE: 30
aacacttccc agagaggatt ctagtctggt aaataaccac agtgtaggaa ctatctaact    60

<210> SEQ ID NO 31
<211> LENGTH: 60
<212> TYPE: DNA
<213> ORGANISM: Artificial
<220> FEATURE:
<223> OTHER INFORMATION: NM_153365
```

<400> SEQUENCE: 31
gaaaactgtg aaactttac cacgacgtaa tctttccagt ctcatactat tttcacaaac    60

<210> SEQ ID NO 32
<211> LENGTH: 60
<212> TYPE: DNA
<213> ORGANISM: Artificial
<220> FEATURE:
<223> OTHER INFORMATION: NM_173079

<400> SEQUENCE: 32
gggcaaaatg tatcactcca aacactactg attcagcatt gttttcatgt cttaaaattg    60

<210> SEQ ID NO 33
<211> LENGTH: 60
<212> TYPE: DNA
<213> ORGANISM: Artificial
<220> FEATURE:
<223> OTHER INFORMATION: NM_203453

<400> SEQUENCE: 33
aagcatagat catttcacct gatgttttg aagcatccta agtacagtag agtagaaaac    60

<210> SEQ ID NO 34
<211> LENGTH: 60
<212> TYPE: DNA
<213> ORGANISM: Artificial
<220> FEATURE:
<223> OTHER INFORMATION: NM_207310

<400> SEQUENCE: 34
ttctagctgt tattttgcta tttggcattt acataaaagc acacgatgaa gcaggtatcg    60

<210> SEQ ID NO 35
<211> LENGTH: 60
<212> TYPE: DNA
<213> ORGANISM: Artificial
<220> FEATURE:
<223> OTHER INFORMATION: NM198485

<400> SEQUENCE: 35
tgcccgtggg agtattggtt tttgagagtc tttttggtac cataagcata tcatccacag    60

<210> SEQ ID NO 36
<211> LENGTH: 60
<212> TYPE: DNA
<213> ORGANISM: Artificial
<220> FEATURE:
<223> OTHER INFORMATION: NM_001267

<400> SEQUENCE: 36
tccatcttcc catgctgcaa tttcttcctg agatttctat aaatataaat gtatgtatgt    60

<210> SEQ ID NO 37
<211> LENGTH: 60
<212> TYPE: DNA
<213> ORGANISM: Artificial
<220> FEATURE:
<223> OTHER INFORMATION: NM_001609

<400> SEQUENCE: 37
cagtgattct caagaaaaag atctcttgcc cattaagaag tgtatcaaaa tctcataagg    60

```
<210> SEQ ID NO 38
<211> LENGTH: 60
<212> TYPE: DNA
<213> ORGANISM: Artificial
<220> FEATURE:
<223> OTHER INFORMATION: NM_002444

<400> SEQUENCE: 38
gcattgctgt gaattagctc acttggtgat atgtcctata ttggctaaat tgaaacctgg    60

<210> SEQ ID NO 39
<211> LENGTH: 60
<212> TYPE: DNA
<213> ORGANISM: Artificial
<220> FEATURE:
<223> OTHER INFORMATION: NM_005794

<400> SEQUENCE: 39
cttcagcaaa gtgtttcatg ggaatgagtc tctctggaag aacttcaagg aacatcatca    60

<210> SEQ ID NO 40
<211> LENGTH: 60
<212> TYPE: DNA
<213> ORGANISM: Artificial
<220> FEATURE:
<223> OTHER INFORMATION: NM_014668

<400> SEQUENCE: 40
gcactctaat ggataacaat ccaagaataa atgattgtaa aagatgatgc cgaagagttg    60

<210> SEQ ID NO 41
<211> LENGTH: 60
<212> TYPE: DNA
<213> ORGANISM: Artificial
<220> FEATURE:
<223> OTHER INFORMATION: NM_015130

<400> SEQUENCE: 41
ctggatgttt agcttcttac tgcaaaaaca taagtaaaac agtcaacttt accatttccg    60

<210> SEQ ID NO 42
<211> LENGTH: 60
<212> TYPE: DNA
<213> ORGANISM: Artificial
<220> FEATURE:
<223> OTHER INFORMATION: NM_015417

<400> SEQUENCE: 42
aaggtttgaa ggttacggct cagggctgcc ccattaaagt cagtgttgtg ttctaaaaaa    60

<210> SEQ ID NO 43
<211> LENGTH: 60
<212> TYPE: DNA
<213> ORGANISM: Artificial
<220> FEATURE:
<223> OTHER INFORMATION: NM_024817

<400> SEQUENCE: 43
tattacataa gcaggtgaaa ggtagaaggc gaattatgtg agtaaatatg gtctgttttc    60

<210> SEQ ID NO 44
<211> LENGTH: 60
<212> TYPE: DNA
<213> ORGANISM: Artificial
<220> FEATURE:
<223> OTHER INFORMATION: NM_033419
```

<400> SEQUENCE: 44
gaaaactttt aaggtgggag ggtggcaagg gatgtgctta ataaatcaat tccaagcctc    60

<210> SEQ ID NO 45
<211> LENGTH: 60
<212> TYPE: DNA
<213> ORGANISM: Artificial
<220> FEATURE:
<223> OTHER INFORMATION: NM_145186

<400> SEQUENCE: 45
catctaagac atgggattca gtgatcatgt ggttctcctt ttaacttaca tgctgaataa    60

<210> SEQ ID NO 46
<211> LENGTH: 60
<212> TYPE: DNA
<213> ORGANISM: Artificial
<220> FEATURE:
<223> OTHER INFORMATION: NM_175887

<400> SEQUENCE: 46
atgttaaact acaaaactgt acagcctatt ttagtgtgga ctattaaaac ccttgcactg    60

<210> SEQ ID NO 47
<211> LENGTH: 60
<212> TYPE: DNA
<213> ORGANISM: Artificial
<220> FEATURE:
<223> OTHER INFORMATION: NM_177433

<400> SEQUENCE: 47
gctattcctt ggagaaggta tttgggattc aattgaagga aattgataag aatgaccact    60

<210> SEQ ID NO 48
<211> LENGTH: 60
<212> TYPE: DNA
<213> ORGANISM: Artificial
<220> FEATURE:
<223> OTHER INFORMATION: NM_178568

<400> SEQUENCE: 48
ggggaacaat gagggcattt catgaaccat ctcaggcact tctgcatcac ggaagacctg    60

<210> SEQ ID NO 49
<211> LENGTH: 60
<212> TYPE: DNA
<213> ORGANISM: Artificial
<220> FEATURE:
<223> OTHER INFORMATION: NM_033419

<400> SEQUENCE: 49
gaaaactttt aaggtgggag ggtggcaagg gatgtgctta ataaatcaat tccaagcctc    60

<210> SEQ ID NO 50
<211> LENGTH: 60
<212> TYPE: DNA
<213> ORGANISM: Artificial
<220> FEATURE:
<223> OTHER INFORMATION: NM_153694

<400> SEQUENCE: 50
ttctttcttc aaagagtcat cagaataaca tggattgaag agacttccga acacttgcta    60

```
<210> SEQ ID NO 51
<211> LENGTH: 60
<212> TYPE: DNA
<213> ORGANISM: Artificial
<220> FEATURE:
<223> OTHER INFORMATION: NM_004448

<400> SEQUENCE: 51
gaaggaacag caatggtgtc agtatccagg ctttgtacag agtgcttttc tgtttagttt      60
```